United States Patent [19]
Ra et al.

[11] Patent Number: 5,874,404
[45] Date of Patent: Feb. 23, 1999

[54] IMMUNOGLOBULIN E RECEPTOR α-CHAIN INHIBITS IGE PRODUCTION AND SECONDARY ALLERGIC RESPONSES

[75] Inventors: Chisei Ra, 14-13, Hanazono 2-chome, Hanamigawa-ku, Chiba-shi, Chiba; Koji Naito; Minoru Hirama, both of Osaka; Ko Okumura, Chiba; Yukiyoshi Yanagihara, Tokyo, all of Japan

[73] Assignees: Chisei Ra, Chiba; The Green Cross Corporation, Osaka, both of Japan

[21] Appl. No.: 238,027

[22] Filed: May 3, 1994

Related U.S. Application Data

[63] Continuation-in-part of Ser. No. 23,912, Feb. 26, 1993, abandoned.

[30] Foreign Application Priority Data

| Aug. 4, 1992 | [JP] | Japan | 4-229227 |
| Aug. 10, 1992 | [JP] | Japan | 4-213002 |
| Oct. 8, 1992 | [JP] | Japan | 4-270513 |
| Oct. 8, 1992 | [JP] | Japan | 4-270514 |
| Oct. 8, 1992 | [JP] | Japan | 4-270515 |
| Jul. 29, 1993 | [JP] | Japan | 5-208217 |
| Aug. 9, 1993 | [JP] | Japan | 5-197341 |
| Oct. 7, 1993 | [JP] | Japan | 5-251605 |
| Oct. 7, 1993 | [JP] | Japan | 5-251606 |
| Oct. 7, 1993 | [JP] | Japan | 5-251608 |
| Oct. 19, 1993 | [JP] | Japan | 5-261355 |
| Oct. 22, 1993 | [JP] | Japan | 5-264802 |

[51] Int. Cl.$^6$ .................................................. A61K 38/00
[52] U.S. Cl. ................................... 514/12; 514/885
[58] Field of Search ................. 514/2, 12; 530/350; 424/125.1

[56] References Cited

U.S. PATENT DOCUMENTS

| 4,962,035 | 10/1990 | Leder | 435/320 |
| 5,011,795 | 4/1991 | Levinson et al. | |

FOREIGN PATENT DOCUMENTS

| 0246967 | 11/1987 | European Pat. Off. . |
| 0336554 | 10/1989 | European Pat. Off. . |
| 0336554 | 11/1989 | European Pat. Off. . |
| 0457527 | 11/1991 | European Pat. Off. . |

OTHER PUBLICATIONS

Stites et al Basic & Clinical Immunology, 1984 pp. 234, 242, Nov. 7, 1997.
P. 21, Basic and Clinical Immunology 1984.
Ra et al. Internal Immunology 5(1): 47, 1993.
Blark et al JBC 266(4): 2639, 1991.
Kochon et al NAR 16(8): 3584, 1988.
*The Journal of Biological Chemistry*, vol. 266, No. 4 (1991), U.Blank et al., "Characterization of truncated a chain products from human, rat, and mouse high affinity receptor for immunoglobulin E", pp. 2639–2646.
*Nucleic Acids Research*, vol. 16, No. 8 (1988), J. Kochan et al., "Isolation of the gene coding for the alpha subunit of the human high affinity IgE receptor" p. 3584.
*Nucleic Acids Research*, vol. 13, No. 8 (1985), Andrea Riccio et al., "The human urokinase–plasminogen activator gene and its Promoter" pp. 2759–2771.
*Biosci. Biotech. Biochem.*, vol. 56, No. 4 (1992), T. Yamauchi et al., "Production of human antithrombin–III in a serum–free culture of CHO cells" pp. 600–604.
*Chemical Abstracts*, vol. 112, No. 23, Jun. 4, 1990, Columbus, Ohio, USA, "Preparation of immunoglobulin E peptide fragments as allergy inhibitors" p. 708, col. 1, No. 217 552x.
*Chemical Abstracts*, vol. 121, No. 13, Sep. 26, 1994, Columbus, Ohio, USA "Preparation of peptides with binding activity to human immunoglobulin E" p. 1086, col. 1, No. 158 211w.
*Journal of Immunology*, vol. 153, No. 8, 15 Oct. 1994, Balt., US, pp. 3804–3810.
*Cellular Immunology*, vol. 151, No. 2, 15 Oct. 1993, pp. 241–256.
*Journal of Immunology*, vol. 148, No. 4, 15 Feb. 1992, Balt., US, pp. 1065–1071.
M.C. Ray, et al., *J. Immunol.*, 131(3): 1096–1102 (1983).
U. Blank, et al., *J. Biol. Chem.*, 266(4), 2639–2646 (1991).
C. Ra, et al., *International Immunology*, 5(1), 47–54 (1993).
U.S. application No. 07/626704, Kinet et al., filed Dec. 14, 1990.
U.S. application No. 07/547892, Kinet, filed Feb. 7, 1990.

*Primary Examiner*—Deborah Crouch
*Assistant Examiner*—Anne Marie S. Beckerleg
*Attorney, Agent, or Firm*—Sughrue, Mion, Zinn, Macpeak & Seas, PLLC

[57] ABSTRACT

Disclosed is an antiallergic composition comprising, as an active ingredient, a peptide which is capable of binding to human IgE, more specifically the high-affinity immunoglobulin E receptor α-chain or a soluble fragment, which is capable of binding to human IgE, or the high-affinity immunoglobulin E receptor α-chain. The composition is clinically useful for blocking allergic responses. An animal model for use in the screening of prophylactic and therapeutic compositions for IgE-related diseases is also disclosed.

6 Claims, 14 Drawing Sheets

FIG. 8
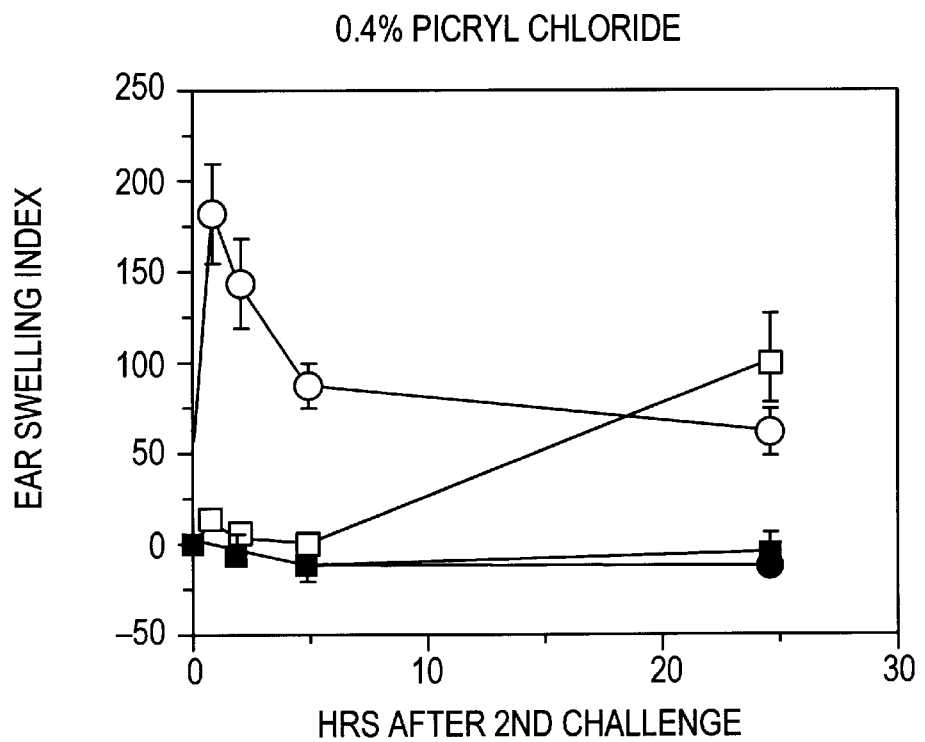
0.4% PICRYL CHLORIDE
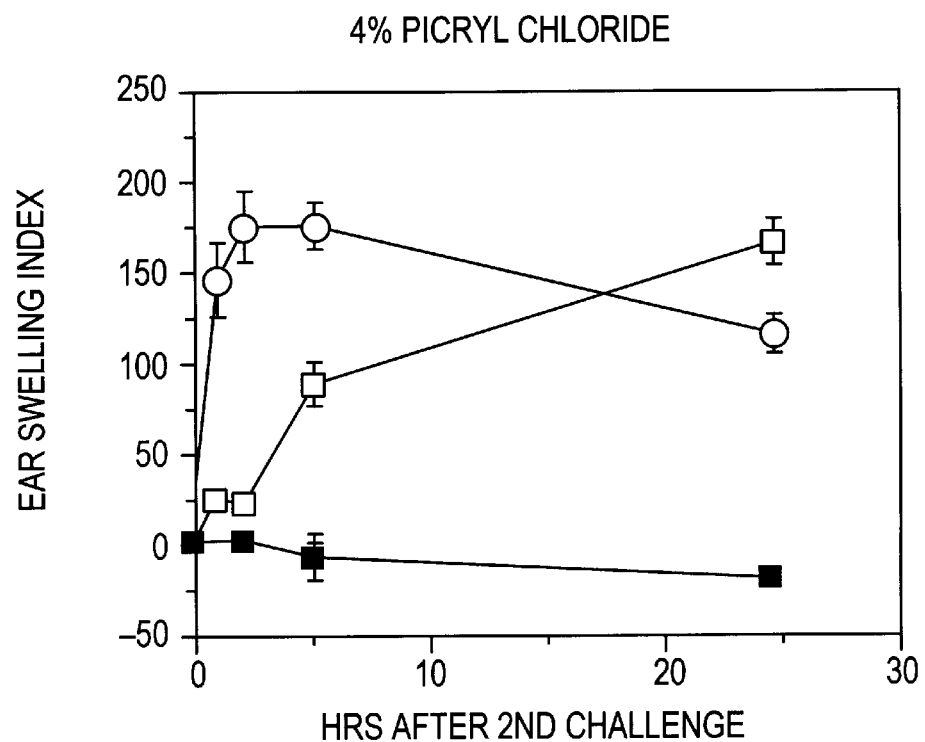
4% PICRYL CHLORIDE

IMMUNOGLOBULIN E RECEPTOR α-CHAIN INHIBITS IGE PRODUCTION AND SECONDARY ALLERGIC RESPONSES

CROSS-REFERENCES TO RELATED APPLICATIONS

This is a continuation-in-part of application Ser. No. 08/023,912 filed on Feb. 26, 1993 which was abandoned on Sep. 17, 1995.

FIELD OF THE INVENTION

The present invention relates to compositions containing, methods of producing and methods of using peptides which are capable of binding to human immunoglobulin E (IgE). More particularly, the invention relates to a prophylactic and/or therapeutic composition for allergic diseases which comprises a high affinity immunoglobulin E receptor α-chain (FcεRIα) or a soluble fragment of such a high affinity immunoglobulin E receptor α-chain (sFcεRIα) which is capable of binding to human IgE. The present invention also relates to a method of preventing or treating an allergic response in human, a process for producing sFcεRIα using genetic engineering techniques and an animal cell carrying a DNA coding for sFcεRIα. The present invention further relates to an animal model for use in the screening of prophylactic and therapeutic compositions for IgE-related diseases. Furthermore, the present invention relates to a method of inhibiting production of IgE.

BACKGROUND OF THE INVENTION

Type I allergy is an inflammatory response which is elicited as the invasion of exogenous agents into the body triggers release of various enzymes and chemical mediators, such as histamine and leukotrienes, from mast cells and eosinophils, which in turn induce tissue-damaging inflammations. The allergic response, when generalized, can lead to a systemic and often life threatening reaction known as anaphylactic shock.

The agents which trigger an anaphylactic shock response include various drugs such as penicillin and insulin, sources of desensitizing allergens such as ticks and fungi, dietary allergens such as eggs and peanuts, iodine-containing contrast media, local anesthetics and so on.

The current pharmacotherapy for anaphylactic shock consists in the administration of epinephrine and steroids. It is reported that if early therapy be judiciously instituted, the prognosis of this condition is generally satisfactory. However, these current treatments are no more than symptomatic remedies and the prophylaxis of anaphylactic shock is considered to be truly important. However, there is no established prophylactic modality for anaphylactic shock, and the current clinical practice appears to be based, at best, on the vague concept of preventing the invasion of high-risk foreign agents.

Therefore, in patients requiring certain drugs, such as penicillin and other antibiotics, and in cases in which an iodine contrast medium is used in X-ray diagnosis, these agents are administered of necessity, even knowing the attendant risk of anaphylactic shock. Thus, there is a pressing need for a positive prophylactic measure against such vigorous immune system responses.

In pollen allergy, symptoms occur preferentially in the nose and eye. Recent years have witnessed a rapid increase in the number of patients who complain of the so-called pollinosis symptoms due to pollens of cedar and other allergenic plants, resulting in, for example, allergic conjunctivitis and allergic rhinitis (eye watering, sinus congestion, nasal congestion, sneezing and the like).

For the prevention of pollen disease, a prophylactic treatment with antiallergic agents, a symptomatic treatment with antihistamines and steroids, and hyposensitization therapy are generally indicated.

However, there is not available as yet an antiallergic agent effective enough as a preventive drug, while the antihistamines and steroids in current use for symptomatic treatment have the problem of side effects.

Atopy provides hereditary basis for allergic responses. The condition is revealed as a congenital hypersensitivity to specific agents, and is usually manifested as bronchial asthma and allergic rhinitis in the patient and his family.

Atopic dermatitis is an inflammatory disease of the skin, which may arise because of a predisposition and which is often characterized by areas of localized itch. It is also known that as the affected area is scratched, the local eruption is aggravated so that the disease runs a chronic course. Moreover, the pruritus associated with atopic dermatitis develops suddenly in many cases and tends to be provoked and intensified by the slightest stimulation.

A variety of treatments have been attempted for atopic dermatitis, but they have proved unsuccessful. The current therapeutic modality for this disease consists of the topical treatment primarily with topical adrenocorticoids and, as an adjunct therapy, antipruritic agents such as antihistamines. But since these drugs are not free from side effects, the advent of a safe and more sure-acting drug for the prevention and treatment of atopic dermatitis has been awaited in earnest.

Patients with bronchial asthma are rapidly increasing in number and presenting a serious problem everywhere in the world today. Bronchial asthma is an airway disease, the cardinal manifestation of which is respiratory distress due to paroxysmal airway constriction, which is life-threatening at times.

While many etiologic agents are usually involved in the onset of bronchial asthma, the chief cause is generally believed to be an increased airway responsiveness due to allergic factors associated with inhaled antigens such as ticks, pollens, dust and so on.

For the treatment of bronchial asthma, prophylaxis with antiallergic drugs and symptomatic treatment with β-receptor stimulants and steroids are practiced today, but there is no antiallergic drug effective enough as a prophylactic. Further, the problem of side effects has been pointed out frequently with the use of β-receptor stimulants and steroids used for symptomatic treatment.

A high affinity immunoglobulin E receptor (FcεRI) is a glycoprotein having a tetrameric structure consisting of an α-chain, a β-chain and two disulfidized γ-chains. It has been reported that a soluble fragment of FcεRI α-chain (sFcεRIα) is produced by genetic engineering techniques using DHFR-deficient CHO cells and that only the extracellular region of the α-chain is involved in the high-affinity binding to IgE [Blank, U. et al., J. Biol. Chem., 266, 2639 (1991)].

Urea-denatured antigen E derived from pollen of Ambrosia and urea-denatured ovalbumin are known to inhibit production of IgE. These urea-denatured antigens inhibit the IgE production reaction by increasing suppressor T cells which suppress helper T cell activity to thereby prevent differentiation of B cells to antibody-producing cells. Suplatast tosilate is also known as a substance capable of inhibiting the IgE produciton. However, these substances have not been put to practical use due to side effects and other problems.

Further, it has not been known so far that peptides capable of binding to IgE directly act on B cells to prevent the IgE production in B cells.

In the development of a drug for the prevention and treatment of IgE-related diseases, a screening of candidate substances is of importance.

One approach to this end comprises inducing an IgE-mediated allergic reaction and checking to see how far this reaction is inhibited. Such approach includes a method comprising the use of animals subjected to passive immunization with purified IgE or animals subjected to active immunization with an antigen as model animals. Both methods are useful but not suited for inducing an allergic reaction repeatedly for investigating the inhibitory effect of test substances.

Thus, in the former method, IgE must be repeatedly administered in order that the allergic reaction may be induced in repetition, with the result that a drug screening cannot be expediently carried out.

The latter method is also disadvantageous in that even though an allergic reaction can be repeatedly induced, not only the antigen-specific IgE but also other antibodies such as the reaction-interfering antigen-specific IgG etc. are produced in the body so that the inhibitory effect on IgE-mediated allergic reaction cannot be accurately estimated.

SUMMARY OF THE INVENTION

An object of the present invention is to provide a clinically useful antiallergic composition which arrests allergic reactions at the rudiment.

The inventors of the present invention have found after much research directed to the above object that the prophylactic administration of a peptide which is capable of binding to human IgE inhibits the onset of allergic diseases. Further, the administration of such a peptide which is capable of binding to human IgE even after development of allergic diseases results in improvement of allergic symptoms. More specifically, the peptide which is prophylactically administered inhibits the IgE production to prevent the attack of type I allergy. Even when the peptide is administered after allergic symptoms are shown, the sumptoms can be ameliolated due to the inhibition of the IgE production. Furthermore, it has been found that in gene amplification using a dihydrofolate reductase (DHFR) gene for the production of sFcεRIα the use of a urokinase (UK) promoter for controlling the expression of the DHFR gene increase an gene amplification level much higher than the prior art level.

Another object of this invention is to provide an animal model which permits repeated observation of IgE-mediated allergic reactions and an expedient method for screening of prophylactic and therapeutic agents for IgE-related diseases.

The above object of the invention can be accomplished by transplanting an IgE-producing hybridoma or myeloma in a appropriate animal.

Having been developed on the basis of the above findings, the present invention relates to an antiallergic composition containing a peptide which is capable of binding to human IqE and to a method of producing sFcεRIα which is comprises transfecting an animal cell with a plasmid (1) carrying a DNA coding for sFcεRIα with a promoter capable of controlling the expression thereof in animal cells and a DHFR gene with a UK promoter or transfecting an animal cell with both a plasmid (2) carrying a DNA coding for sFcεRIα with a promoter capable of controlling the expression thereof in animal cells and a plasmid (3) carrying a DHFR gene with a UK promoter, and culturing the animal cells.

The present invention further provides an animal model for use in the screening of prophylactic and therapeutic compositions for IgE-related diseases.

BRIEF DESCRIPTION OF THE DRAWINGS

In FIG. 4, ○, Δ, □ and ● each stand for one of the four runs.

In FIG. 6, - □ - stands for control group (n=7), - ○ - for $10^6$ IGELa2-transplanted group (n=7) and - ● - for $10^7$ IGELa2-transplanted group (n=7).

In FIG. 7, - ○ - stands for 0.4% picryl chloride (PC)-challenged untransplanted group (n=12), - ● - for 4% PC-challenged untransplanted group (n=12), - □ - for 0.4% PC-challenged IGELa2-transplanted group (n=12), - ■ - for 4% PC-challenged IGELa2-transplanted group (n=11).

FIG. 8 shows the time course of ear swelling in the second antigen-challenged mice obtained in Test Example 6-A-(3). The mice used in the experiment of FIG. 7 were challenged again 6 days later. In FIG. 8, - ○ - stands for IGELa2-transplanted twice challenged group (n=6), - □ - for untransplanted twice challenged group (n=6), - ● - for IGELa2-transplanted once challenged group, - ■ - for untransplanted once challenged group.

In FIG. 9, column A stands for untransplanted group (n=12), B for a2-transplanted group (n=12), C for a2.1-transplanted group (n=6), D for a2.3-transplanted group (n=6), E for a2.4-transplanted group (n=6), F for a2.15-transplanted mice (n=6) and G for a2.16-transplanted group (n=6).

In FIG. 10, column A stands for 0.4% PC-challenged untransplanted group (n=12), column B for 0.4% PC-challenged transplanted group (n=12), column C for OX-challenged transplanted group (n=6) and column D for FITC-challenged transplanted group (n=6).

In FIG. 11, - □ - stands for sFcεRIα-treated IGELa2-transplanted group, - ○ - for sFcεRIα-treated untransplanted group, - ■ - for untreated IGELa2-transplanted group and - ● - for untreated untransplanted group.

In FIG. 12, * means that the difference-is statistically significant (p <0.05, paired t-test).

In FIG. 13, lanes 1 and 4 stand for control, lanes 2 and 5 for 10 ng/ml of sFcεRIα and lanes 3 and 6 for 100 ng/ml of sFcεRIα.

DETAILED DESCRIPTION OF THE INVENTION

Figure 1:
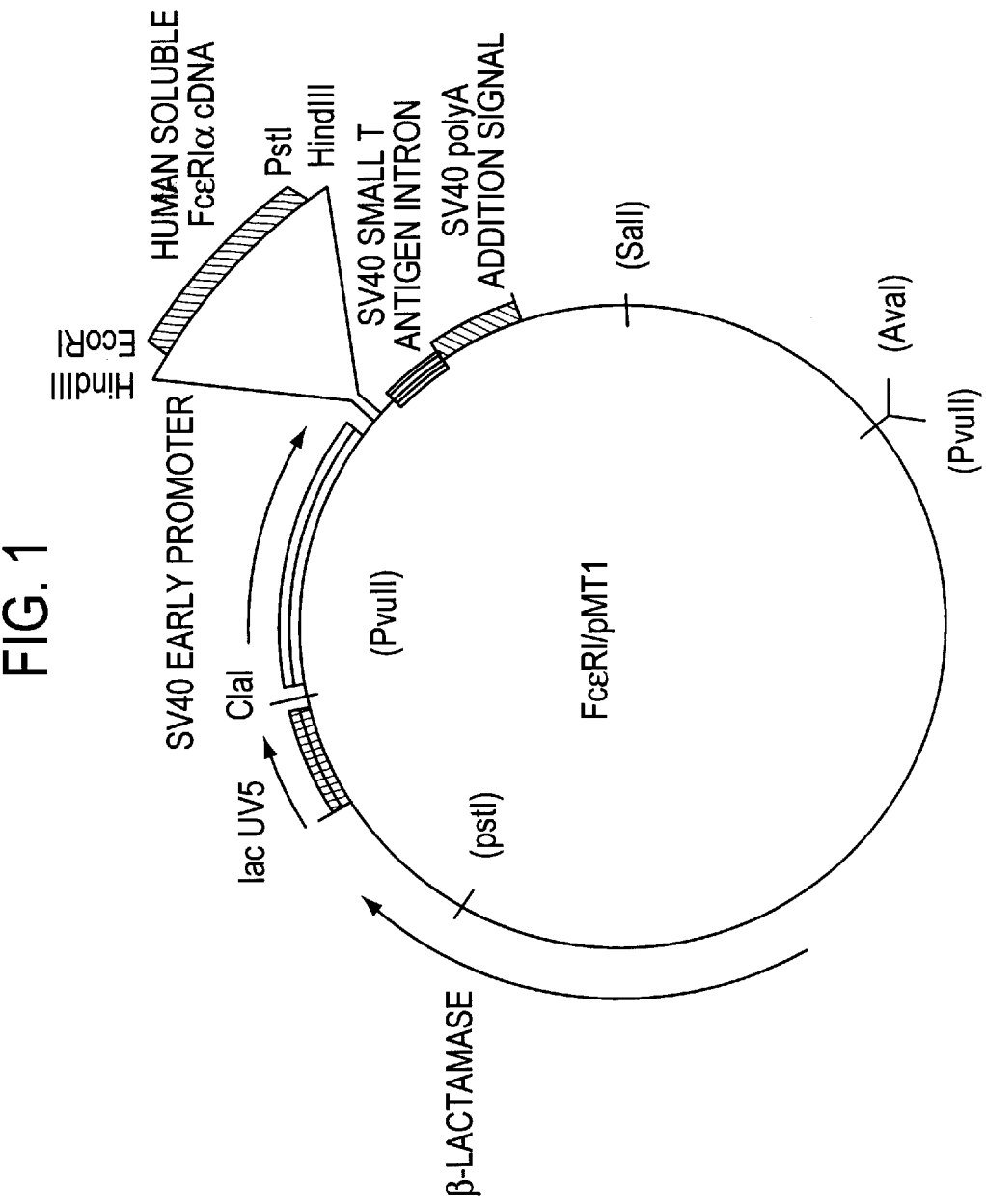
FIG. 1 illustrates the structure of a plasmid designated as FcεRI/pMT1.

The term "peptide which is capable of binding to human IgE" as used herein means a peptide which specifically binds to human IgE to inhibit its function. Any peptide is usable in the present invention as long as it shows about 80% IgE inhibition in the IgE inhibition assay as described below. Specific examples include a peptide containing a high affinity immunoglobulin E receptor α-chain (FcεRIα) and a peptide containing a soluble fragment of such a high affinity immunoglobulin E receptor α-chain (sFcεRIα) which are capable of binding to human IgE.

The above-mentioned peptides inhibit the binding of IgE to the high affinity immunoglobulin E receptor (FcεRIα) which specifically binds to the Fc moiety of IgE, on the cell membranes of mast cells and eosinophils and, therefore, arrest allergic reactions at the source.

FcεRIα stands for the α-chain of said FcεRI, and sFcεRIα stands for the extracellular region of the α-chain.

A peptide which is capable of binding to human IgE for use in the present invention, need only contain at least the extracellular region of the α-chain, viz. sFcεRIα, and both FcεRIα and FcεRI may likewise be employed with success. Mutants artificially derived by a genetic engineering technique and a derivative for drug delivery system, for example, the conjugate with albumin, can also be used if the mutant is capable of binding to human IgE, but sFcεRIα is particularly desirable. Preferably, the peptides are obtained and derived from humans.

sFcεRIα can be produced by tissue culture or by genetic engineering. The process for producing sFcεRIα according to the present invention is described in detail below.

[I] Plasmid (1)

Plasmid (1) carrying a DNA coding for sFcεRIα with a promotor capable of controlling the expression thereof in animal cells and a DHFR gene with a UK promoter can be prepared by inserting (i) a DNA coding for sFcεRIα with a promotor capable of controlling the expression thereof in animal cells upstream therefrom and (ii) a DHFR gene with a UK promoter upstream therefrom into a plasmid. Plasmid (1) is constructed so that a DNA coding for a heterologous protein, sFcεRIα, functions under the control of a promoter capable of controlling the expression thereof in animal cells.

Examples of such a promoter include a promoter of polyoma, adenovirus 2 or, in most cases, simian virus 40 (SV40) origin. The early or late promoters of SV40 is particularly useful since they can be obtained readily from the virus as a fragment containing the replication origin of SV40 [Fiers et al., Nature, 273, 113 (1978)], A DNA fragment of SV40 about 250 bp containing from the HindIII site to the BglI site in the replication origin can be also used. Further, any promoter and regulatory sequence (enhancer) related to the heterologous protein gene can also be used as long as they function in a host cell.

Usable as a promoter-enhancer to be used in the expression vectors for use in animal cells are the promoter-enhancer of the SV40 early or late gene, the adenovirus 2 major late promoter region, the globulin enhancer-promoter region, the LTR of RNA viruses, the metallothionein promoter region, the β-actin promoter and the like. As for the origin of replication, one derived from SV40 or some other virus (e.g. polyoma, adeno, VSV, BPV) may be inserted into the vector employed, or the replication mechanism of the host cells chromosome may be used. If the vector is integrated into the host cell chromosome, the latter is enough.

Further, plasmid (1) in constructed so that a DHFR gene functions under the control of the UK promoter added upstream therefrom. Both of the UK promoter and the DHFR gene are known. The former is described in Nucl. Acids Res., 13, 2759-2771 (1985), etc. and the latter is described in JP-A-59-192089, JP-A-63-105675, etc. (the term "JP-A" used herein means an unexamined published Japanese patent application).

Any human sFcεRIα can be used as long as it exhibits activity of the high affinity immunoglobulin E receptor. An example of a DNA coding for human sFcεRIα is one described in Kochan et al., Nucl. Acids Res., 16, 3584 (1988).

In plasmid (1), a unit of a DNA coding for human sFcεRIα and a promotor capable of controlling the expression thereof in animal cells and a unit of the DHFR gene and the UK promotor may be inserted in the same direction of in the reverse direction. Plasmid (1) may further contain the replication origin, the ribosome-binding site or the RNA splicing site upstream from a DNA unit of a DNA coding for human sFcεRIα and a promotor capable of controlling the expression thereof in animal cells, the polyA addition site or the transcription termination sequence downstream from the DNA unit.

[II] Plasmids (2) and (3)

Plasmid (2) contains a DNA coding for human sFcεRIα and a promotor capable of controlling the expression thereof in animal cells and plasmid (3) contains the DHFR gene and the UK promoter. These plasmids contain the same DNA unit as described in the above [I]-(i) and (ii), respectively, and are used to cotransfect animal cells for the expression of human sFcεRIα.

[III] Transfectants

Transfectants according to the present invention can be obtained by transfecting animal cells with plasmid (1) described in the above [I] or cotransfecting animal cells with plasmids (2) or (3) as described in the above [II]. Usable as the animal cell line are Green monkey kidney cell line (VERO), HeLa cells, Chinese hamster ovary (CHO) cell line, W138, newborn hamster kidney cell line (BHK), CV-1 Origin SV40 cell (COS-7), MDCK cell line, C127, HKG, human kidney cell line and the like. Specific examples thereof include CHO-K1 (ATCC CCL61), BHK (ATCC CCL10), COS-7 (ATCC CRL1651), VERO (ATCC CCL81), among others. Particularly preferred are those cells deficient in the DHFR gene.

Transfection of animal cells can be carried out by the conventional method such as calcium phosphate precipitation method, protoplast polyethylene glycol fusion method, electropolation or the like.

DNA amplification using methotrexate (MTX) can be carried out by culturing the transfectants in a medium containing MTX in a concentration of 10 nM to 10 μM and selecting the MTX resistant cells from the cells which can grow in the medium. MTX may be added stepwise to the medium or added in high concentration in a single step.

Examples of the medium include MEM-α supplemented with 1 to 10% fetal calf serum (FCS), Dulbecco's modified MEM (D-MEM) and the like. Cultivation of the transfectants can be carried out at 10° to 37° C. for 1 to 200 hours.

[IV] Production of heterologous protein

The transfectants described in the above [III] are cultivated to cause expression of human sFcεRIα gene by the known methods.

The production of sFcεRIα by genetic engineering may be carried out by using *E. coli* or yeasts instead of the above-mentioned animal cells.

The polypeptides of the present invention can be obtained by art-recognized methods, for example, cell lysis and purification or mere purification from the culture medium in those instances in which secretion has occurred. Standard purification methods can be used, such as chromatography, dialysis, affinity chromatography, combinations thereof, and the like. A particularly suitable method is affinity chromatography wherein an IgE antibody is affixed to a chromatography matrix. The solution containing the target polypeptides is passed over the matrix and bound molecules, including the target protein are eluted from the matrix, for example, by using high ionic strength buffer.

The peptide which is capable of binding to human IgE can be applied as a systemic therapy or as a topical therapy.

For systemic treatment, the peptide is dissolved in physiological saline for injection or distilled water for injection and administered parenterally, preferably intravenously. The dosage form may be a liquid or a lyophilizate and can be manufactured by the methods well known in the art.

For topical administration, various dosage forms for external application to the skin or mucosa such as ocular mucosa, nasal mucosa, bronchial mucosa, etc. can be utilized.

The antiallergic composition of the present invention can also be administered in other dosage forms and routes of administration, chosen according to types of allergy to be prevented or treated.

For the prevention or therapy of pollen allergy, ophthalmic and nasal solutions or ointments may prove of benefit. Any of such pharmaceutical preparations can be manufactured by the known manufacturing method.

For example, an ophthalmic or nasal solution can be manufactured by dissolving the active ingredient peptide which is capable of binding to human IgE in distilled water for injection, adding any auxiliary agent required, such as a buffer, isotonizing agent, thickener, preservative, stabilizer, surfactant, antiseptic, etc., and adjusting the mixture to pH 4 to 9. A nasal spray can be manufactured for example by the method described in JP-A-63-101318.

The ointment which may be used in the present invention is preferably a gel ointment. Such an ointment can be manufactured, for example, by mixing the active ingredient peptide which is capable of binding to human IgE with a gel base prepared by using a carboxyvinyl polymer and, as a basic thickener, sodium hydroxide or the like and, after addition of auxiliary agents as necessary, adjusting the mixture to pH 4 to 9.

The topical dermatologic preparation for the prophylaxis and/or therapy of atopic dermatitis includes, a cream, a gel ointment and a lotion. Any of these preparations can be manufactured by using the peptide which is capable of binding to human IgE in combination with a water-soluble high molecular compound, an oil, white petrolatum, lower alcohol or the like. If necessary, adding auxiliary agents such as a buffer, isotonizing agent, thickener, preservative, stabilizer, surfactant, lubricant, preservative and so on, may be added.

A prophylactic-therapeutic composition for bronchial asthma can be prepared in a dosage form which is suitable for topical application to the bronchial mucosa or nasal mucosa. A typical procedure comprises dissolving the peptide of the invention in an appropriate solvent such as a physiological saline and injectable solutions and packing the peptide solution into a spray device for aerosol inhalation.

The composition can be used for both prophylaxis and symptomatic control. The dosage is dependent on the type of disease and the patient's age, sex and condition. In normal human serum, IgE circulates at a concentration of about 3 ng/ml, which is based on a molecular weight of 185,000, corresponding to about $10^{10}$ IgE molecules per ml of serum. In serum of patients suffered from allergic diseases, the IgE concentration raises to 100 to 10,000 times as high as that in normal human serum. For example, the IgE concentration in serum of patients suffered form hay fever, allergic rhinitis or atopic asthma is about 300 ng/ml ($10^{12}$ molecules/ml), and that in atopic dermatitis patient is about 30 µg/ml ($10^{14}$ molecules/ml). For prophylactic treatment, it is preferable to administer at least twice the amount of IgE corresponding to the exogenous factor. For symptomatic control, it is preferable to use a massive dose soon after onset, preferably at least 10-fold as great a dose relative to the amount of IgE corresponding to the exogenous factor. The dosage for therapeutic purpose is considered preferably not less than 500 µg/kg.

For use as a prophylactic treatment for anaphylactic shock, the peptide of the invention may be administered once or twice a day beginning several days, e.g. 4 days, prior to administration of a drug or contrast medium.

According to the present invention, human sFcεRIα can be produced in a large quantity. The thus obtained human sFcεRIα can be formulated into various dosage forms which are suitable for use as clinically useful antiallergic compositions which arrest allergic reactions at the rudiment.

The mechanism of inhibition of the allergic reaction by the peptide capable of binding to human IgE according to the present invention has been elucidated as described in Test Example 7 below. Thus, the peptide binds to membrane-bound IgE on activated B cell and is taken into the cell to specifically inhibit the IgE production, thereby arresting type I allergic reactions at the rudiment.

The animal model for use in the screening of prophylactic and therapeutic composition for IgE-related diseases according to the present invention is described in detail below.

There is virtually no limitation on the species of such animal and the mouse, rat, guinea pig and rabbit, among others, can be employed.

There is virtually no limitation, either, on the kind of hybridoma or myeloma to be transplanted as long as it is not rejected by the recipient animal and remains viable in its body.

It is not essential that such hybridoma or myeloma establish itself perpetually in the host body but all that is necessary is that it may remain viable during the test period.

Examples of the hybridoma include IGELa2 (TIB142), IGELb4 (TIB141) and SE-1.3 (HB137) and an example of the myeloma is U266B1 (TIB196).

The means for constructing the animal model is not critical but the following procedures are recommended.

First, the method comprising transplanting a suspension of an IgE-producing hybridoma or myeloma in a syngenic animal may be mentioned; For example, the procedure of transplanting IGELa2 hybridoma (anti 2,4,6-trinitrophenyl) (ATCC No. TIB142) in BALB/c mice, IGELb4 hybridoma (anti 2,4,6-trinitrophenyl) (ATCC No. TIB141) in (C57BL/

6×BALB/c)F$_1$ mice or (BALB/c×C57BL/6)F$_1$ mice, or SE-1.3 hybridoma (Anti phenylarsonate) (ATCC No. HB137) in (A/J×BALB/c)F$_1$ mice or (BALB/c×A/J)F$_1$ mice may be mentioned. The hybridoma or myeloma is suspended in Hanks' solution, PBS and the like.

Secondly, the method comprising transplanting an IgE-producing hybridoma or myeloma in a congenitally immunodeficient animal may be mentioned. Transplantation into nude mice or SCID mice is a typical example.

Thirdly, the method comprising transplanting an IgE-producing hybridoma or myeloma in an animal artificially rendered immunodeficient by X-ray or other treatment may be mentioned.

The site of transplanting an IgE-producing hybridoma or myeloma is not critical but the cells are preferably inoculated subcutaneously at the back or intraperitoneally.

The inoculum size of an IgE-producing hybridoma or myeloma is generally $10^3$–$10^{10}$ and preferably $10^5$–$10^8$ cells per 200 μl.

In the animal model according to the invention, an IgE-mediated allergic reaction can be repeatedly induced by repeating an antigen challenge so that a screening of prophylactic and therapeutic agents for IgE-related diseases can be efficiently and expediently carried out.

Specifically, the antigen challenge induces ear edema when directed to the ear, conjunctivitis-like symptoms when directed to the eye, or rhinitis-like symptoms when directed to the nasal cavity, thus allowing a screening to be carried out using the inhibition of any of such responses as the indicator.

The following reference, test, and working examples illustrate the invention in further detail. However, they are not to be construed as limiting the scope of the invention.

EXAMPLE 1
Production of sFcεRIα
[I] Construction of FcεRI/pMT1
[Construction of a plasmid using a DNA coding for the human sFcεRIα chain with a promoter (SV40) capable of controlling the expression of said chain in an animal cell].

cDNA library was prepared using mRNA extracted from human basophilic precursor cell KU812 and phage vector λgt11 (Promega). The resulting cDNA library was screened by plaque hybridization using a synthetic probe prepared in accordance with the method reported by Kochan et al. [Nucl. Acids Res., 16, 3584 (1988)] to obtain the full length of cDNA coding for human FcεRIα.

The full length human FcεRIα-encoding cDNA was digested with EcoRI and SduI to obtain a 685 bp DNA fragment. This EcoRI-SduI fragment was ligated with synthetic nucleotides complementary to SEQ ID NO:1 and SEQ ID NO:2. The synthetic nucleotides contain a TAA stop codon which corresponds to TAA at the 26th to 28th bases of the base sequence of SEQ ID NO:1 and TTA at the 6th to 8th bases of SEQ ID NO:2, and a BamHI site. The EcoRI-BamHI fragment obtained by this ligation was inserted into the EcoRI-BamHI cleavage site in plasmid pGEM-3Z (Promega) to obtain plasmid FcεRI/pGEM-3Z. A HindIII site was created between the EcoRI site and T7 promoter in FcεRI/pGEM-3Z and then, a HindIII fragment containing human sFcεRIα cDNA was isolated from this plasmid. The HindIII fragment thus obtained was inserted into the HindIII site (downstream from SV40 early promoter) of plasmid pko [K. V. Doren et al., J. Virol., 50, 606 (1984)]. Thus, an expression vector FcεRI/pMT1 (FIG. 1) having human FcεRIα leader sequence-human sFcεRIα gene inserted therein was constructed. SEQ ID NO:3 shows a DNA sequence coding for said human sFcεRIα (including 5' noncoding region) and an amino acid sequence deduced therefrom.

[II] Construction of pTT06
[Construction of a plasmid using a DNA coding for dihydrofolate reductase (DHFR) with the urokinase (UK) promoter].

Figure 2:
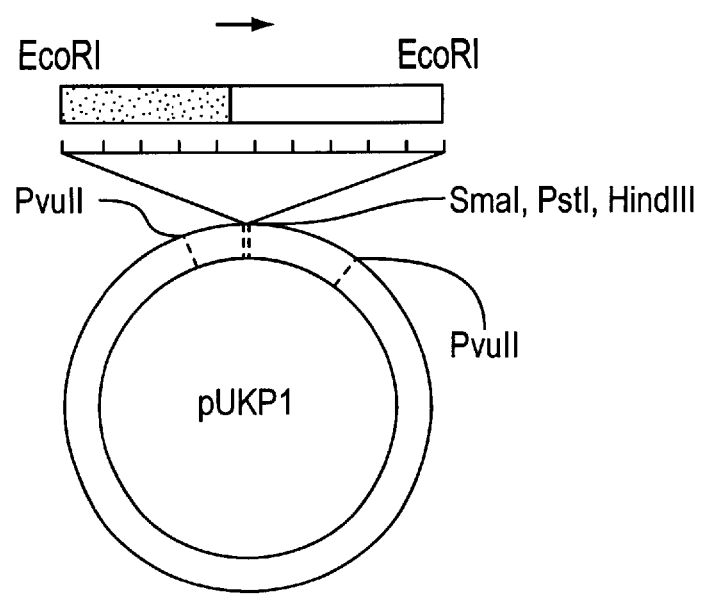
FIG. 2 illustrates the structure of the subcloned pUKP1.

A plasmid, pTT06, containing the UK promoter, DHFR cDNA and SV40 polyA was constructed as described below in accordance with the method described in Biosci. Biotech. Biochem., 56(4), 600–604 (1992) (cf. FIG. 2 and FIG. 3).
(i) Construction of pUKP1: preparation of DNA encoding UK promoter
(1) Preparation of probe Plasmid pUK4 containing a part of human urokinase cDNA (JP-A-61-177987) was digested with PstI and about 400 bp DNA fragment was isolated by 1% agarose gel electrophoresis followed by electroelution. A 0.4 μg portion of this fragment was labeled with [α-$^{32}$P]dCTP (Amersham, PB10205) using MultiPrime Kit (Pharmacia).

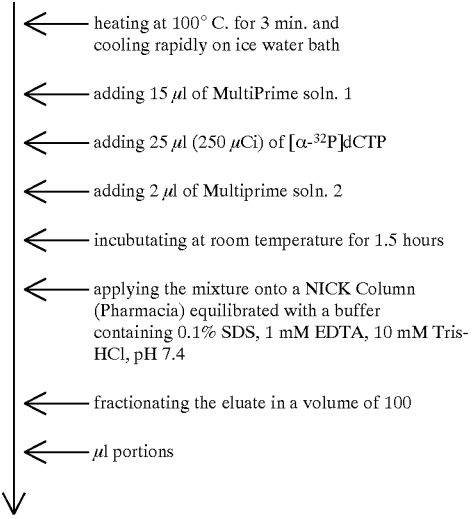

The desired fractions were combined and measured for Cerenkov count and it was found that the Cerenkov count was 9.69×10$^7$ cpm. The labeling efficiency and specific radioactivity were calculated as 41% and 2.4×10$^8$ cpm/μg, respectively.
(2) Southern hybridization of DNA derived from HKG cells According to Riccio et al., Nucl. Acids Res., 13, 2759–2771 (1985), the human urokinase promoter region is obtained as a 5.8 kb EcoRI fragment and a 12 kb BamHI fragment from human chromosomal DNA. A DNA of HKG cells was digested independently with EcoRI and BamHI. A 10 μg portion of each digests was subjected to 0.8% agarose gel electrophoresis followed by the Southern hybridization using the probe prepared in the above (1). As a result, a signal was detected at the position corresponding to each of the desired fragment sizes.
(3) Preparation of 5.8 kb EcoRI fragment 200 μg of high molecular weight DNA of HKG cell was digested with 1,000 units of EcoRI overnight at 37° C. The resulting digests were subjected to 0.8% agarose gel electrophoresis (Electrophoretic device HE-102, Takara Shuzo) using λ-DNA digested with HindIII as a marker and the gel was stained with ethidium bromide. The gel was excised in a length of 2 mm around the position corresponding to 5.8 kb. The upper and lower parts thereof were also excised in a length of 3 mm. The resulting gel portions were subjected to electroelution to extract DNA fragments. A part of the extracted DNA fragments was subjected to 0.8% agarose gel electrophoresis followed by the Southern hybridization in order to confirm as to whether or not the desired DNA fragments were included in the extracted DNA fragments. As a result, it was assumed that the DNA fragment extracted from the gel of 2 mm around the 5.8 kb position contained the desired urokinase promoter region.

(4) Preparation of DNA library and screening

DNA library of the DNA extracted in the above (3) was prepared using phage vector λgt10. A total of 6.5×10^5 recombinant phages were subjected to primary screening by plaque hybridization. As a result, 28 positive clones were obtained. The positive clones were subjected to secondary screening to thereby obtain 5 positive clones. DNA was extracted from the recombinant phages which gave positive clones by the simplified extraction method. The extracted DNA was digested with EcoRI and the digests were subjected to 1% agarose gel electrophoresis followed by the Southern hybridization. The results of the Southern hybridization revealed that two recombinant phages were positive.

(5) Subcloning of 5.8 kb EcoRI fragment

A phage DNA was extracted from the clone, which was confirmed to be positive by the Southern hybridization, by the simplified extraction method. The extracted DNA was digested with EcoRI and the digests were extracted with phenolchloroform. The aqueous layer was further extracted with chloroform and the extract was precipitated with ethanol. The resulting phage DNA fragments digested with EcoRI were ligated with a 1 μg portion of pUC9 (Pharmacia) which was digested with EcoRI and subsequently treated with alkaline phosphatase. The resulting ligation products were used to transform *E. coli* HB101. Some of the transformed cells were subjected to the simplified extraction method to extract plasmid DNA, which was digested with EcoRI and electrophoresed on 1% agarose gel. As a result, it was found that several subclones contained a 5.8 kb DNA fragment. Two clones were digested with various restriction enzymes and the digests were subjected to 1% agarose gel electrophoresis. These clones showed different cleavage sites, but contained several identical fragments. Thus, it was assumed that the 5.8 kb DNA fragment was inserted into the respective clones in the different directions. These plasmids were named as pUKP1 (FIG. 2) and pUKP2, respectively.

(6) Digestion of pUKP1 with restriction enzymes

It was examined as to whether or not pUKP1 contained the DNA fragments expected to be contained in view of the restriction enzyme cleavage map deduced from the base sequence of human urokinase reported by Riccio et al (supra).

*E. coli* HB101 carrying pUKP1 was cultured in 100 ml of Superbroth containing 40 μg/ml of ampicillin overnight at 37° C. and the plasmid DNA was isolated from the cells by the alkali-SDS method. The thus obtained plasmid DNA was subjected to digestion with various restriction enzymes. Table 1 shows the DNA fragments expected to be contained in pUKP1, sizes of the fragments, and the presence or absence of the fragments. As shown in Table 1, all the expected fragments were found in pUKP1. Therefore, it was confirmed that the DNA fragment coding for the desired human urokinase promoter region was cloned.

TABLE 1

| Restriction enzyme | Sizes of fragment (bp) | Presence or absence of fragment |
| --- | --- | --- |
| BglII | 270 | o* |
| SmaI | 2266 | o |
| PvuII | 695 | o |
|  | 1641 | o |

TABLE 1-continued

| Restriction enzyme | Sizes of fragment (bp) | Presence or absence of fragment |
| --- | --- | --- |
|  | 792 | o |
| PstI | 682 | o |
|  | 946 | o |
|  | 584 | o |
| HindIII | 1817 | o |
| SmaI + EcoRV | 590 | o |
| EcoRI + EcoRV | 3050 | o |
| HindIII + EcoRV | 1283 | o |
| BamHI + BglII | 595 | o |
| BglII + EcoRV | 2205 | o |

*Note: o means the presence of the expected fragment.

(7) Confirmation of a part of the base sequence of pUKP1

A part of the base sequence of the plasmid DNA as obtained in the above (6) was determined by the dideoxy method. As a result, the base sequence thus determined was in agreement with that reported by Riccio et al (supra).

(ii) Construction of pTT06

[Construction of plasmid containing UK promoter, DHFR cDNA and SV40 PolyA]

Figure 3:
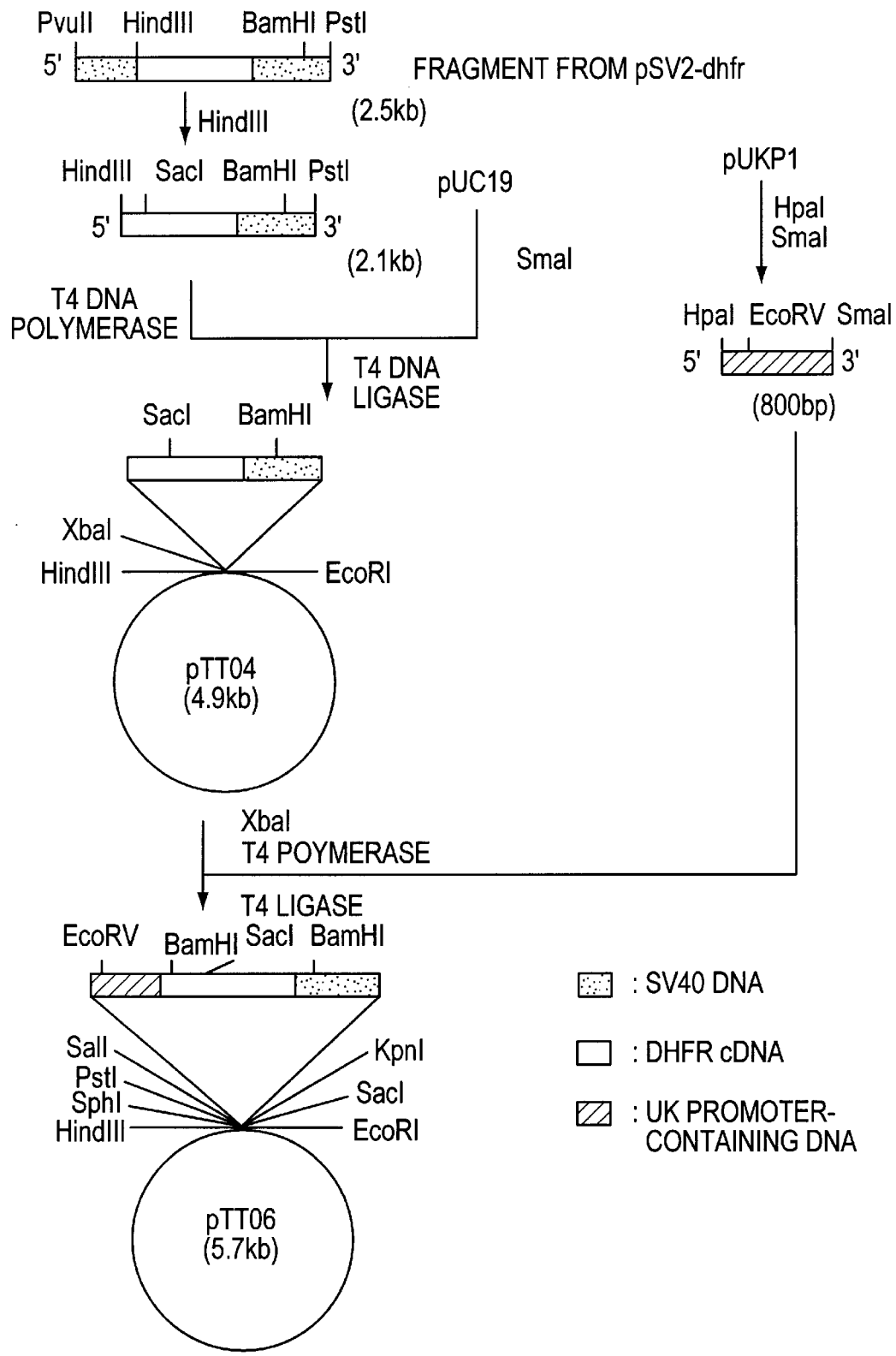
FIG. 3 illustrates the scheme for constructing the plasmid designated as pTT06.

Plasmid pTT06 was constructed in the following manner (FIG. 3).

pSV2-dhfr (JP-A-63-105675) was digested with PvuII and PstI to obtain a DNA fragment of 2.5 kb containing SV40 enhancer-promoter, DHFR cDNA and SV40 late polyA addition signal. The resulting DNA fragment was further digested with HindIII so as to delete the SV40 enhancer-promoter region. The thus obtained HindIII-PstI fragment of 2.1 kb was treated with T4 DNA polymerase to render the both ends blunt and inserted into the SmaI site of pUC19 (Takara Shuzo) for cloning. pTT06 thus obtained contained DHFR cDNA in such a manner that the 5' end (the N terminal of the protein) of DHFR cDNA was joined to the HindIII site of the pUC19 polylinker. In order to examine as to whether or not pTT04 was a desired plasmid, pTT04 was digested with BamHI to give a DNA fragment of from the BamHI site in the pUC19 polylinker to the BamHI site downstream from the SV40 late polyA addition signal. Thus, a DNA fragment of 1.6 kb was obtained. Then, pUKP1 was digested with HapI and SmaI to obtain a DNA fragment of about 800 bp containing from the SmaI site at about 30 bp downstream from the transcription initiation site of the urokinase gene to the HpaI site at about 800 bp upstream from the transcription initiation site. This DNA fragment containing the UK promoter was inserted into the upstream site of DHFR cDNA. Namely, pTT04 was digested with XbaI and the digestion product was treated with bacterial alkaline phosphatase (BAP) and then blunt-ended with T4 DNA polymerase. The resulting fragment was ligated with the HpaI-SmaI fragment containing the UK promoter. After transformation, the clones in which the DHFR gene and the UK promoter were inserted in the same transcription direction were selected. Subsequently, the plasmid which gave a 280 bp DNA fragment containing from the EcoRV site in the vicinity of the 5' side of the UK promoter region originated in pTT04 to the SalI site originated in pUC19 was selected and named as pTT06. The structure of pTT06 was examined by digestion with EcoRV and SalI, and EcoRV and BamHI. pTT06 gave 0.9 kb, 1.8 kb and 2.9 kb fragments by digestion with EcoRV and SacI and 0.6 kb, 1.6 kb and 3.5 kb fragments by digestion with EcoRV and BamHI. These fragments having such sizes were in agreement with the desired ones expected from the restriction enzyme cleavage map of the plasmid.

[III] Introduction into animal cells and establishment of a high-productivity cell strain
(i) Materials
Plasmid DNA FcεRI/pMT1: The plasmid produced by incorporating the human FcεRIα chain leader sequence and the sFcεRIα chain gene into plasmid pko.

pTT06: The plasmid containing a DHFR gene expression unit placed under the control of the UK promoter (5' upstream regulatory region comprising about 8,000 bp and containing the urokinase gene transcription initiation site).

Cells: The cell line CHO DXB-11 (DHFR-deficient strain).

Prepared and multiplied by the method described by G. Urlaub et al. in Proc. Natl. Acad. Sci. USA, 77, 4216–4220 (1980).

Methotrexate (MTX): A 2 mM stock solution was prepared by dissolving (+)Amethopterin (Sigma) in 0.14M NaCl+0.02M HEPES (Nacalai Tesque). This solution was added to the medium to a predetermined concentration.

(ii) Procedure
(1) DNA introduction and transfectant supernatant assaying for expression DHFR-deficient CHO DXB-11 cells subcultured using Eagle's MEM-a (ribonucleic acid- and deoxyribonucleic acid-free) supplemented with 10% FCS were detached from the dish by treatment with trypsin (0.25%) and suspended in Hanks' solution to a density of $10^7$ cells/ml. The plasmid DNAs (1 μg of pTT06 and 40 μg of FcεRI/pMT1) were simultaneously introduced into 5 ×$10^6$ cells (0.5 ml of the suspension) by electropolation. After cultivation in Eagle's MEM-α (ribonucleic acid- and deoxyribonucleic acid-free) supplemented with 10% FCS, the resultant colonies were picked and cultured. The spent culture medium of the transfectants was assayed for human sFcεRIα chain activity by the method described below under (2) and strains showing high activity were used for DNA amplification using MTX.

2) Assaying of the soluble human FcεRIα chain

The soluble human FcεRIα chain concentration was determined in terms of the degree of inhibition of binding of $^{125}$I-labeled mouse IgE to FcεRI occurring on a rat basophilic cell line. The materials and procedure used were as follows. (Materials)

Cells: The rat basophilic cell line RBL-2H3 [Barsumian, B. L. et at., Eur. J. Immun., 11, 317–323 (1981)] was cultivated in Eagle's MEM containing 10% FCS, 100 U/ml penicillin and 100 μg/ml streptomycin.

IgE: Anti-dinitrophenyl mouse monoclonal IgE [HI-DNP-E-26-82; Liu, F. T. et al., J. Immunol., 124, 2728–2737 (1980)] or anti-trinitrophenyl (TNP) mouse monoclonal IgE was used. The anti-TNP mouse monoclonal IgE was purified from the culture supernatant of the hybridoma IGELb4 (ATCC No. TIB141) or mouse ascitic fluid with the same IGELbH cells.

Iodine-labeling of IgE: The Bio-Rad Enzymobeads method was used. A mixture was prepared from 50 μl of 0.2M phosphate buffer (pH 7.2), 10 μl of mouse monoclonal IgE (2.14 mg/ml), 50 μl of Enzymobeads reagent, 25 μl of Na$^{125}$I (95 MBq) and 25 μl of a 1% aqueous solution of β-D-glucose. The reaction was carried out at room temperature for 15–20 minutes. After admixing with 150 μl of phosphate-buffered physiological saline containing 10 mg/ml tyrosine, 10% glycerol and 0.1% xylene cyanole, protein recovery was effected by gel filtration using a PD-10 column (Pharmacia).
(Procedure)

IgE binding assay:
1) Since CHO cells are maintained using the 10% FCS-supplemented Eagle's MEM-α (ribonucleic acid- and deoxyribonucleic acid-free), samples were prepared by diluting with this culture medium (125–250 μl).

2) $^{125}$I-Labeled IgE diluted with Dulbecco's phosphate buffered physiological saline supplemented with 3% bovine serum albumin and 0.1% NaN$_3$ (PBS/3% BSA) was added to each sample prepared in 1). The whole volume was 500 μl and the concentration of $^{125}$I-labeled IgE was 100 ng/ml. This mixture was incubated at room temperature for 3–6 hours.

3) To said mixture was added 50 μl of a suspension of RBL-2H3 cells (3–8×$10^7$ cells/ml) in PBS/3% BSA, followed by 1–2 hours of incubation on ice. In an unlabeled IgE group used for assessing nonspecific adsorption of labeled IgE on cells, a mixture of 150 μl of the RBL-2H3 cell suspension and 15 μl of 2.1 mg/ml unlabeled IgE was prepared in advance. This mixture (55 μl) was added to the mixture prepared in step 2).

4) Cells were caused to settle as a sediment by centrifugation (1,000 rpm, 5 minutes) and the supernatant was discarded.

(5) The cells were rinsed once with PBS/3% BSA and the bound radio-activity was measured using a gamma counter.

(6) The cpm value obtained by adding Eagle's MEM-α (ribohucleic acid- and deoxyribonucleic acid-free) supplemented with 10% FCS was used as a control (the additive-free case) and the percent binding inhibition was calculated as follows:

$$\text{Binding inhibition (\%)} = \frac{\text{Radioactivity in additive-free case} - \text{Radioactivity in test group}}{\text{Radioactivity in additive-free case} - \text{Radioactivity in IgE-added group}} \times 100$$

(3) Amplification of the inserted gene using MTX

Dishes (10 cm) containing 8–10 ml of a selective medium containing 10 nM MTX were inoculated with a human sFcεRIα chain-producing strain obtained as described in (2) to a density of 5–10×$10^5$ cells/dish. Cultivation was continued for 2–4 weeks while performing medium exchange at intervals of about 3 days. Thereby, a sufficient number of 10 nM MTX-resistant cells were obtained. The cells were transferred to a medium at the next MTX concentration level. In this way, the MTX concentration was increased stepwise for gene amplification, starting from 10 nM MTX, to 50 nM, 100 nM, 200 nM, 500 nM, 1 μM, 2 μM, 4 μM and 10 μM.

(4) Cloning of soluble human FcεRIα chain producers

Among the human sFcεRIα chain producers obtained after gene amplification using MTX as described in (3), several strains were subjected to cloning by the limiting dilution method. Thus, cells resistant to each concentration of MTX were cultured in Eagle's MEM-α (ribonucleic acid- and deoxyribonucleic acid-free) supplemented with 10% FCS and 2–10 μM MTX and distributed into the wells of a 96-well plate. Cells were recovered from wells showing cell proliferation and transferred to a 24-well plate and then, further, to a 10 cm dish. At the stage of confluence, the production of the human sFcεRIα chain in each supernatant was determined. Culture supernatant of 38.4.3 cells in the 24-well plate showed 0.7% of IC$_{50}$. On the assumption that a binding ratio of the human sFcεRIα to IgE was 1:1 in the IgE binding assay, it was calculated that the human sFcεRIα was produced in an amount of 1.8 mg per 1 liter of the culture supernatant of 38.4.3 cells. The yield of the human sFcεRIα of each cells was shown in Table 2.

TABLE 2

|  | Yield of human sFcεRIα | |
| --- | --- | --- |
| Clone | Supernatant in 24-well plate* (mg/l) | Supernatant in 10-cm dish* (mg/l) |
| 38.4.2 | 1.6 | 4.0 |
| 38.4.3 | 1.8 | 4.5 |
| 58.2.8 | 1.3 | 3.9 |
| 58.2.7 | 1.7 | 5.1 |
| 66.2.2 | 1.5 | 4.4 |
| 19.10.23 | 2.1 | 4.6 |

*average of the amounts of the product from the culture supernatant in two different concentrations

[IV] Purification of the human sFcεRIα chain

Figure 4:
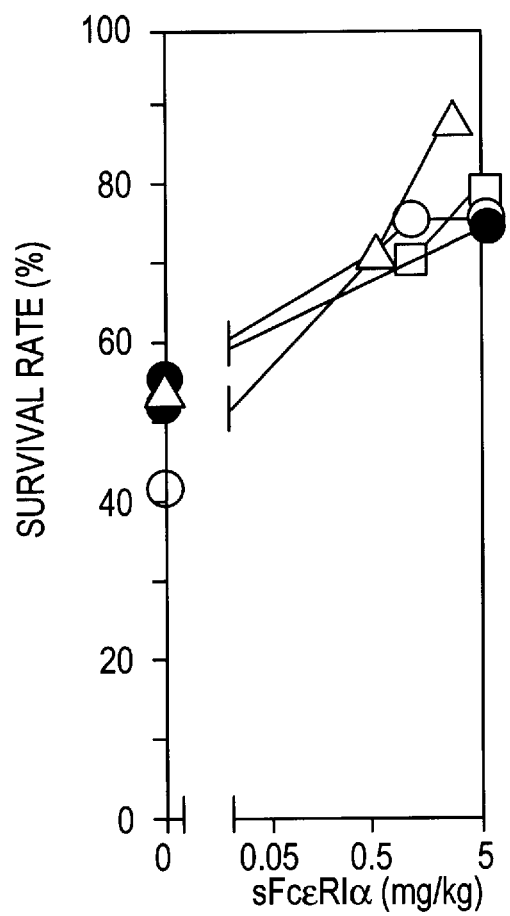
FIG. 4 graphically shows the results of Test Example 5.

To 983 ml of the culture supernatant derived from a cloned cell strain 38.4.3 showing a relatively high production of the human sFcεRIα chain was added a 1/20 volume of 1 mM Tris, pH 8.0, together with 10 mM banzamidine, 10 mM ethylenediaminetetraacetic acid and 0.02% sodium azide. The mixture was filtered (0.22-μm filter) and the filtrate was purified using an IgE-Sepharose 4B column [prepared by binding 10 mg of anti-trinitrophenyl IgE purified from a mouse hybridoma IGELb4 (ATCC No. TIB141) culture supernatant to 1 g of activated CH Sepharose (Pharmacia) in 0.1M sodium hydrogen carbonate]. The column was washed with PBS containing 0.02% sodium azide. The protein bound to the column was eluted with an eluant comprising 0.2M acetic acid, 0.2M sodium chloride and 0.02% sodium azide, pH 2.8. The thus purified human sFcεRIα chain was dialyzed against 10 mM ammonium hydrogen carbonate, and 200 μl of the dialyzate was dried in SpeedVac and checked by SDS electrophoresis. Upon staining with Coomassie Brilliant Blue, a distinct band was detected at a position corresponding to a molecular weight of about 50 kDa, without any other protein band, under reducing conditions as well as under nonreducing conditions (FIG. 4). This protein had an activity of inhibiting the binding of radio-labeled IgE to basophilic cells (RBL-2H3 cells; vide supra). The concentration of such purified human FcεRIα chain was determined by the method of Bradford [Bradford, M. M., Anal. Biochem., 72, 248 (1976)].

EXAMPLE 2

Composition for administration by injection or spraying

In distilled water for injection were dissolved 100 mg of the purified human sFcεRIα and 100 mg of glucose to give a purified human sFcεRIα concentration of 2 mg/ml. The solution was filtered using a 0.45-μm membrane filter and the filtrate was aseptically distributed into 5-ml vials, followed by nitrogen gas charging and tight closure to give a composition for intravenous injection or for spraying.

EXAMPLE 3

Ophthalmic solution

In distilled water for injection were dissolved 500 mg of the purified human sFcεRIα, 50 g of sorbitol and 20 mg of methyl parahydroxybenzoate. The pH was adjusted to 6.5 with phosphate buffer and the whole volume was made to 1,000 ml. The solution was filtered using a 0.45 μm membrane filter and the filtrate was aseptically distributed into eye drop bottles. Thus was prepared an ophthalmic solution.

EXAMPLE 4

Composition for nasal administration

A composition for nasal administration was prepared in the same manner as in Example 3.

EXAMPLE 5

Ointment

To 25.0 parts by weight of a 2% aqueous solution of a carboxyvinyl polymer (Carbopol 940, product of Goodrich) was added gradually 25 parts by weight of a 2% aqueous solution of sodium hydroxide with stirring. Further stirring gave a gel-like composition.

A solution of 2 parts by weight of the purified human sFcεRIα in an appropriate amount of purified water was added to said gel-like composition, followed by further addition of purified water to make the whole amount 100 parts by weight. The subsequent uniform stirring gave an ointment.

EXAMPLE 6

Ointment

White petrolatum (60 parts by weight), 1 part by weight of polyoxyethylene cetyl ether and 1 part by weight of aluminum stearate were melted and mixed up with heating. While maintaining the mixture at about 75° C., 5 parts by weight of sorbitan monostearate and 10 parts by weight of purified water were added thereto. The mixture was stirred and then cooled to about 45° C. and 5 parts by weight of the purified human sFcεRIα in an appropriate amount of purified water was added thereto. The subsequent stirring gave an ointment.

Test Example 1

Effect on anaphylactic shock in actively sensitized rats

The test was performed by the method of Levine et al. [Levine, B. B. et al., Int. Arch. Allergy Appl. Immunol., 39, 156 (1979)]. ICR rats were sensitized by intraperitoneal administration of a solution of 10 μg of DNP-Ascaris in an Al(OH)$_3$ gel (2 mg/ml). Four weeks after sensitization, the animals were given the human sFcεRIα-containing injection prepared as described above in Example 1 by intravenous injection two times at a dose of 100 μg/kg/day. Twenty-four hours after administration, anaphylactic shock was induced by intravenous administration of DNP-ovalbumin (10 mg/kg) and animal deaths within 24 hours were counted (n=5). While 4 animals died in the control group, no animals died in the human sFcεRIα group.

Test Example 2

Effect on allergic conjunctivitis in mice

BALB/C mice were sensitized by intraperitoneal administration of a solution of 10 μg of DNP-Ascaris in a 2 mg/ml Al(OH)$_3$ gel. Four weeks following sensitization, 0.1 ml of the ophthalmic solution prepared as described above in Example 3 was administered to each eye by instillation once daily for a week. On the next day, 0.1 ml of a 0.5% DNP-ovalbumin solution was instilled in each eye. While hyperemia and edema of the ocular conjunctiva, namely signs of conjunctivitis, were observed in the control group of mice, no such signs were observed in the group of mice given human sFcεRIα. Administration of the above-mentioned ophthalmic solution by instillation to the control group mice that had showed such symptoms as mentioned above ameliorated the symptoms.

Test Example 3

Effect on atopic dermatitis

The ointment prepared as described above in Example 5 was applied once daily to the rough skin of pediatric patients with atopic dermatitis. After several weeks of application, the rough skin began to return to normal, with the itchy sensation subsiding. Application of the ointment did not cause any observable signs of skin irritation, for example rash.

Test Example 4
Inhibition of bronchial constriction in actively sensitized guinea pigs Evaluation was performed by the Konzett-Rossler method [H. Konzett and R. Rossler: Naunyn-Schmiedbergs Arch. Pharmakol., 195, 71 (1940)]. Male Hartley guinea pigs were sensitized with ovalbumin (50 mg/kg, intraperitoneal administration). Fourteen days later, the guinea pigs were anesthetized with pentobarbital (70 mg/kg, intraperitoneal administration) and their spontaneous respiration was arrested using succinylcholine (2 mg/kg, intraperitoneal administration). The trachea of each animal was cannulated and respiration was maintained under a positive pressure using a small-sized artificial respirator (5 ml/breath, 87 breaths/minute, 10 cm water). The constrictive response of the bronchus was expressed in terms of the amplified mobile area of tracing on a physiological recorder of the outflow of air into the lung as measured by an air flow meter connected in series with a differential pressure transducer. The human sFcεRIα-containing composition for injection as prepared in Example 1 was intravenously administered at a dose of 50 μg/kg. An hour later, ovalbumin was intravenously administered (300 μg/kg). It was found that administration of human sFcεRIα significantly inhibited the constrictive response of the bronchus in the guinea pigs.

Test Example 5
Effect on anaphylaxis in mice which have received passive immunization The test was carried out in the following manner with reference to the method described in M. Pittman, F. G. Germith, Jr., Proc. Soc. Exptl. Biol. Med., 87, 425 (1954).

Pertussis vaccine ($2 \times 10^9$ cells) was intraperitoneally administered to female 8-week-old ICR mice (15 to 20 mice per group). Two days later, each mouse was intraperitoneally given 2 μg of anti-TNP mouse monoclonal IgE which had been prepared from a mouse hybridoma IGELb4 (ATCC TIB141). Twenty-four hours after the IgE sensitization, human sFcεRIα (0–5 mg/kg) was intravenously administered to the mice. Seventy-two hours after the IgE sensitization (48 hours after the administration of human sFcεRIα), the mice were challenged with an antigen by intravenously given TNP-HSA (50 μg).

The survival rate of the mice sixty minutes following the challenge with an antigen was determined in accordance with the following calculation.

$$\text{Survival rate (\%)} = \frac{\text{Number of survival mice}}{\text{Total number of mice}} \times 100$$

The same experiment was repeated four times. As shown in FIG. 4, it was found that the survival rate was increased by the administration of human sFcεRIα.

Test Example 6
Inhibitory effect on secondary allergic reaction in mice
A. Construction of the animal model Female BALB/c mice (aged 8 weeks) were inoculated with $10^6$ or $10^7$ cells of the anti-TNP.IgE-producing hybridoma IGELa2 (ATCC No. TIB142) subcutaneously at the back to construct an animal model.
(1) Determination of anti-TNP.IgE level in mouse blood The blood anti-TNP.IgE in the IGELa2-transplanted mice as prepared above was serially determined by EIA. EIA was carried out using a TNP-HSA-coated plate (10 μg/ml, 50 μl/well) as follows.

The test serum obtained from the IGELa2-transplanted mice and untreated mice (control) (7 mice per group) was diluted 30–3750-fold with 1% BSA/TBS and 50 μl aliquots were distributed to the plate and incubated at 4° C. overnight. The plate was then washed with 0.9% NaCl/0.05% Tween 20 and the bound anti-TNP.IgE was detected using POD-labelled sheep anti-mouse IgE (1:1000, The Binding Site Ltd.) and 1 mg/ml o-phenylenediamine/0.006% $H_2O_2$. As the purified IgE standard, the IgE purified from a culture supernatant of anti-TNP.IgE-producing hybridoma IGELb4 (ATCC No. TIB141) was used.

Figure 5:
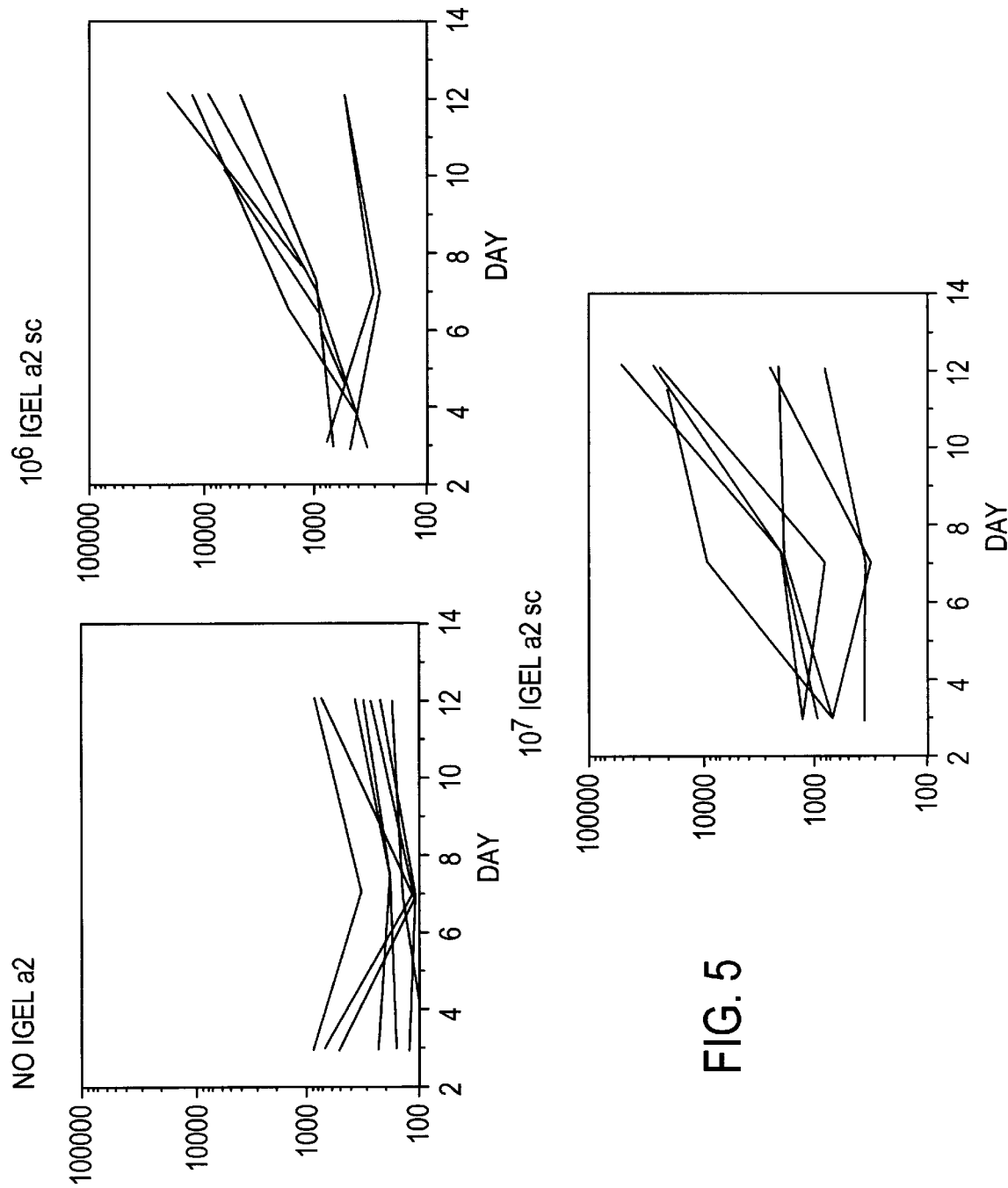
FIG. 5 graphically shows the results of anti-TNP.IgE level in mouse blood obtained in Test Example 6-A-(1).

The results are shown in FIG. 5. The blood anti-TNP.IgE level rose with time in the $10^6$ hybridoma-transplanted mice but was not elevated in the control mice. A similar result was obtained in mice inoculated with $10^7$ cells of the hybridoma.
(2) Determination of the time course of ear swelling in antigen-challenged mice (I)

Mice were inoculated with $10^6$ or $10^7$ IGELa2 cells subcutaneously at the back in the same manner as described above. On day 8 after inoculation, 10 μl of 4% picryl chloride in acetone was applied to the left ear of the mice and untreated mice (antigen challenge) and the time course of ear swelling was determined. The difference between the thickness of the ear before the challenge and that after the challenge was used as the index. Determinations were made using diameter gauge PEACOCK available from Ozaki Seisakusho.

Figure 6:
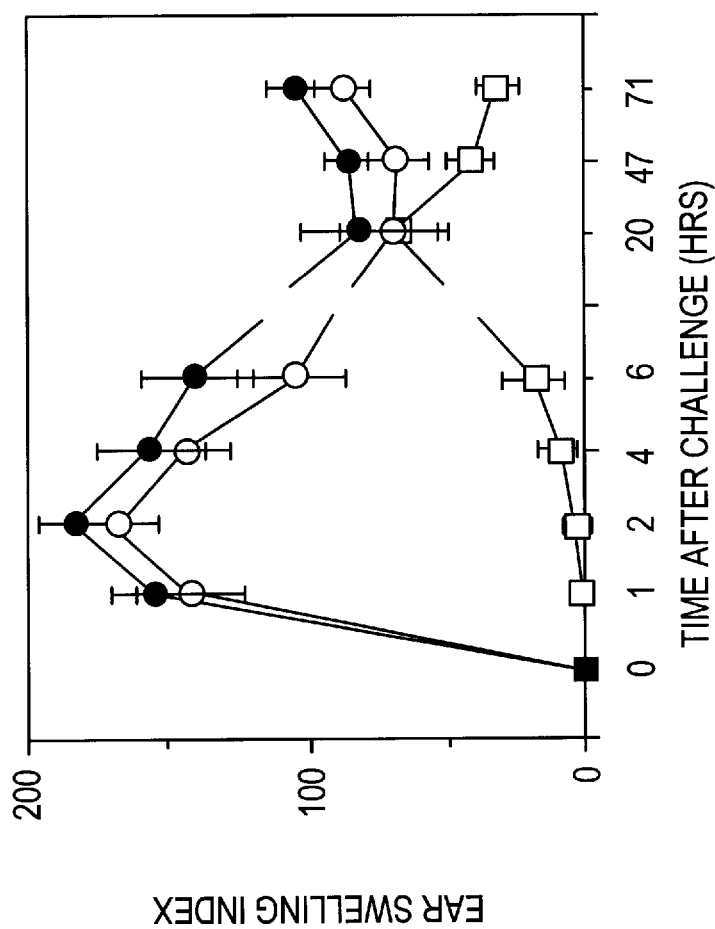
FIG. 6 shows the time course of ear swelling in antigen-challenged mice obtained in Test Example 6-A-(2).

The results are shown in FIG. 6. Whereas ear swelling became maximal in 1–2 hours after antigen challenge in the hybridoma-transplanted mice, no swelling was observed within 1–2 hours after antigen challenge in the unoperated mice. In mice inoculated with $10^7$ hybridoma cells, ear swelling also became maximal in 1–2 hours after antigen challenge.

The above finding of the maximal ear swelling occurring 1–2 hours after antigen challenge in hybridoma-transplanted mice indicated that the efficacy of an antiallergic agent can be estimated from the degree of inhibition of ear swelling during this time period.
(3) Determination of the time course of ear swelling in antigen-challenged mice (II)

As in the above (2), mice were inoculated with $10^6$ hybridoma cells and the first antigen challenge was carried out using 0.4% or 4% picryl chloride (PC) solution on day 8 after inoculation. Control mice were also subjected to antigen challenge.

Figure 7:
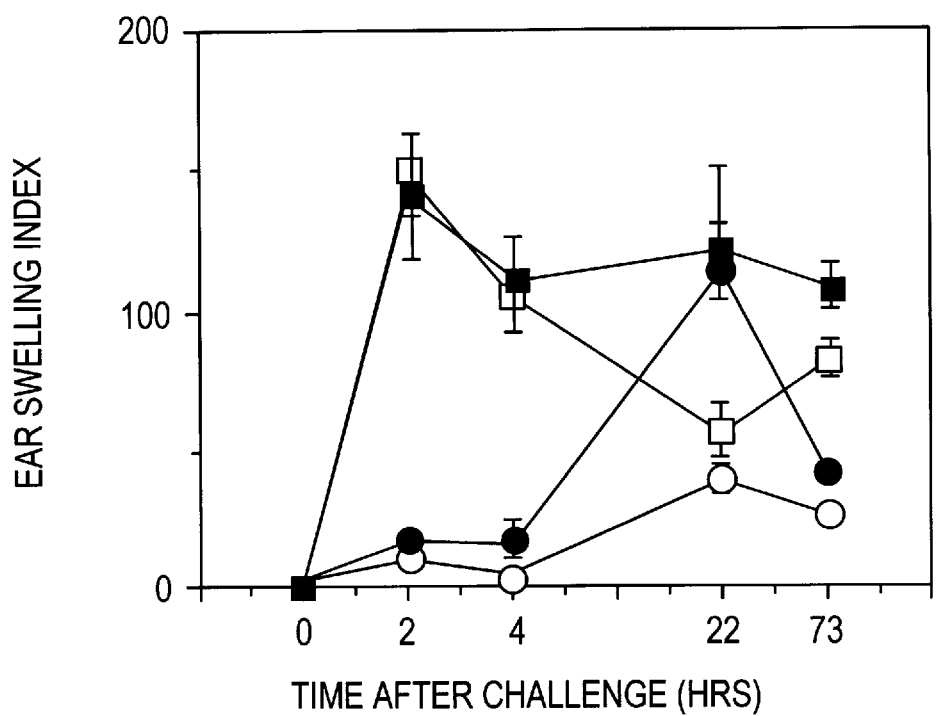
FIG. 7 shows the time course of ear swelling in the first antigen-challenged mice obtained in Test Example 6-A-(3).

The results are shown in FIG. 7. It was found that ear swelling became maximal in 2 hours after antigen challenge just as in the above (2).

Then, on day 6 after the first antigen challenge, the second antigen challenge was performed in the same manner as the first challenge and using the index described in the above (2), the time course of ear swelling was investigated.

The results are shown in FIG. 8. In the hybridoma-transplanted mice, ear swelling became maximal in 2 hours just as after the first antigen challenge and the index value was substantially equal to that at 2 hours after the first challenge. In contrast, the control mice showed no swelling of the ear.

The above results indicate that even if the antigen challenge is performed more than once at the same site in hybridoma-transplanted mice, ear swelling may be repeatedly induced with good reproducibility.

The results further indicate that the use of such hybridoma-transplanted mice not only enables confirmation of the preventive and inhibitory effect of antiallergic agents on primary allergic reaction but also confirmation of the preventive and inhibitory effect on allergic reactions due to the second and subsequent exposures to the antigen.

(4) Proof of anti-TNP-IgE-related type I allergy (i) As in the above (1), mice were inoculated with $10^6$ hybridoma cells subcutaneously at the back. As hybridomas, the above-mentioned IGELa2 and its subclones a2.1, a2.3, a2.4, a2.15 and a2.6 were used. Of these hybridomas, IGELa2, a2.4 and a2.16 were anti-TNP.IgE-producers, but neither IGEL a2.1, a2.3 nor a2.15 secreted anti-TNP.IgE. Antigen challenge was carried out in the same manner as in the above (2) and the index value was determined 2 hours after the challenge.

Figure 9:
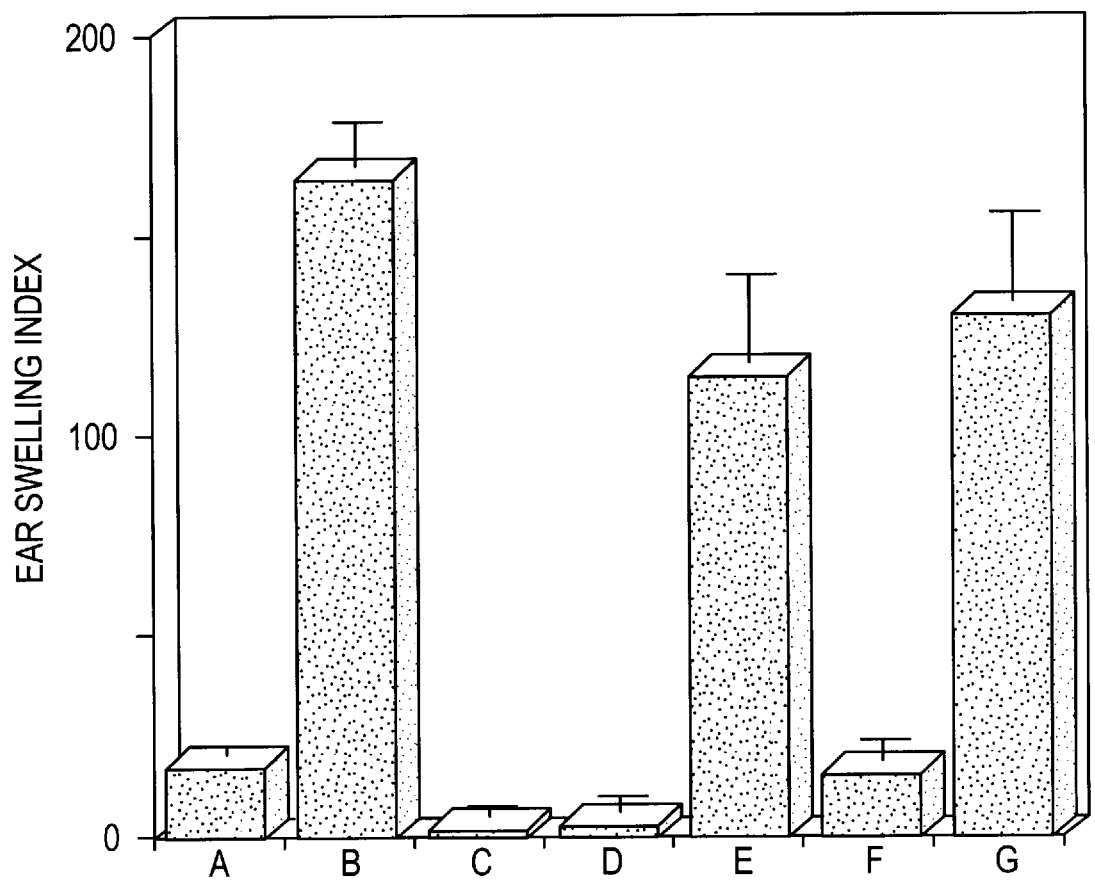
FIG. 9 is a graph showing ear swelling in IgE-producing cells or non-producing cells-transplanted mice obtained in Test Example 6-A-(4)-(i).

The results are shown in FIG. 9. As shown in FIG. 9, ear swelling was observed with the anti-TNP.IgE producers only. It was, therefore, clear that the anti-TNP.IgE is essential to ear swelling.

(ii) Antigen challenge in IGELa2-transplanted mice was carried out using, respectively, 1% oxazolone (OX) and 1% fluorescein isothiocyanate (FITC) as well as 0.4% picryl chloride (PC).

Figure 10:
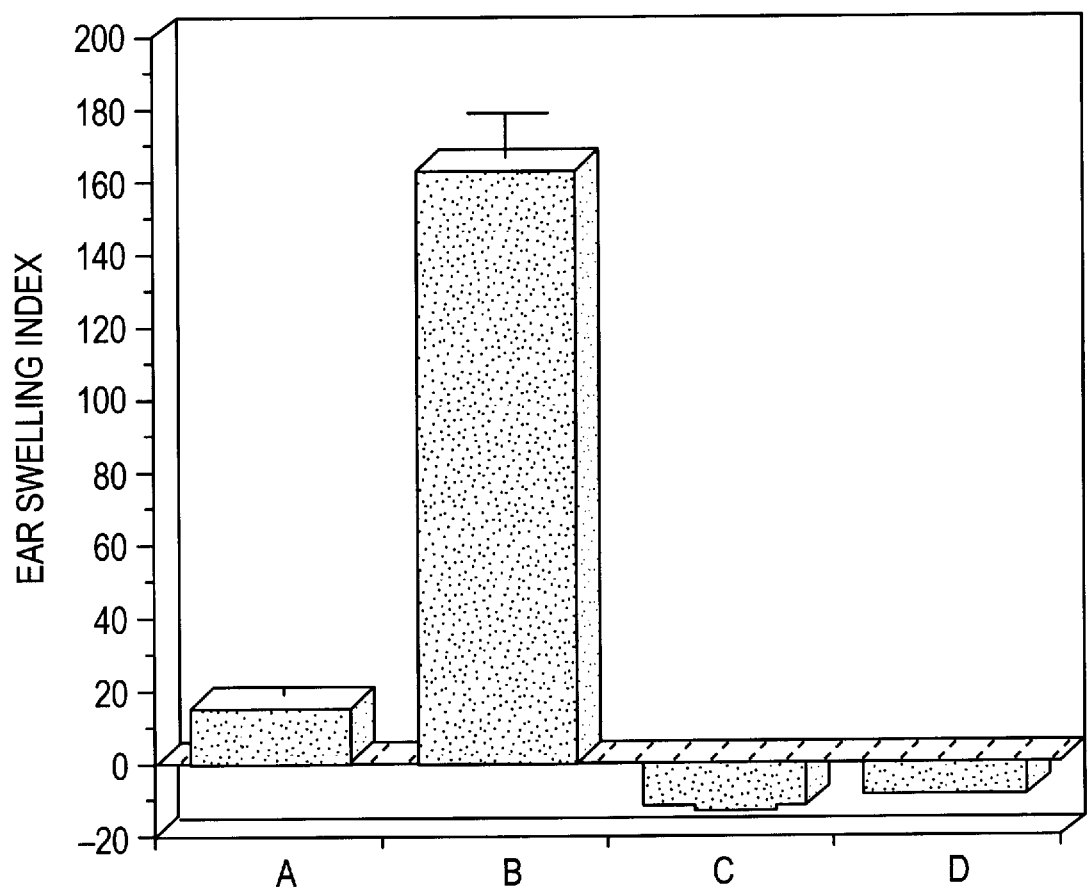
FIG. 10 is a graph showing ear swelling in oxazolone (OX),- fluorescein isothiocyanate (FITC) or PC-challenged IGELa2-transplanted mice obtained in Test Example 6-A-(4)-(ii).

The results are shown in FIG. 10. As shown in FIG. 10, ear swelling was observed only in challenges with picryl chloride and not found with the other antigens. This result indicates that ear swelling requires a specific antigen which is recognized by IgE.

From the results obtained in (i) and (ii), it was found that ear swelling in this assay is an anti-TNP.IgE-mediated type I allergic reaction.

The animal model we constructed allows an allergic reaction to be induced more often than once after a single inoculation with hybridoma cells and is of great use in the screening of antiallergic agents.

B. Inhibitory effect of sFceRIα on secondary allergic reaction

As in the above A-(3), the first antigen challenge was carried out by applying 10 μl of 0.4% picryl chloride-acetone to the left ear of mice on day 8 after hybridoma transplantation and the second antigen challenge was carried out in the same manner on day 14.

On the other hand, sFceRIα was administered intravenously in a dose of 25 μg/mouse on days 7 and 8 after transplantation and in a dose of 100 μg/mouse on days 9, 11, 13 and 15. PBS was administered to the control group in place of sFceRIα.

The effect of sFceRIα was evaluated using the index described in the above A-(2).

Figure 11:
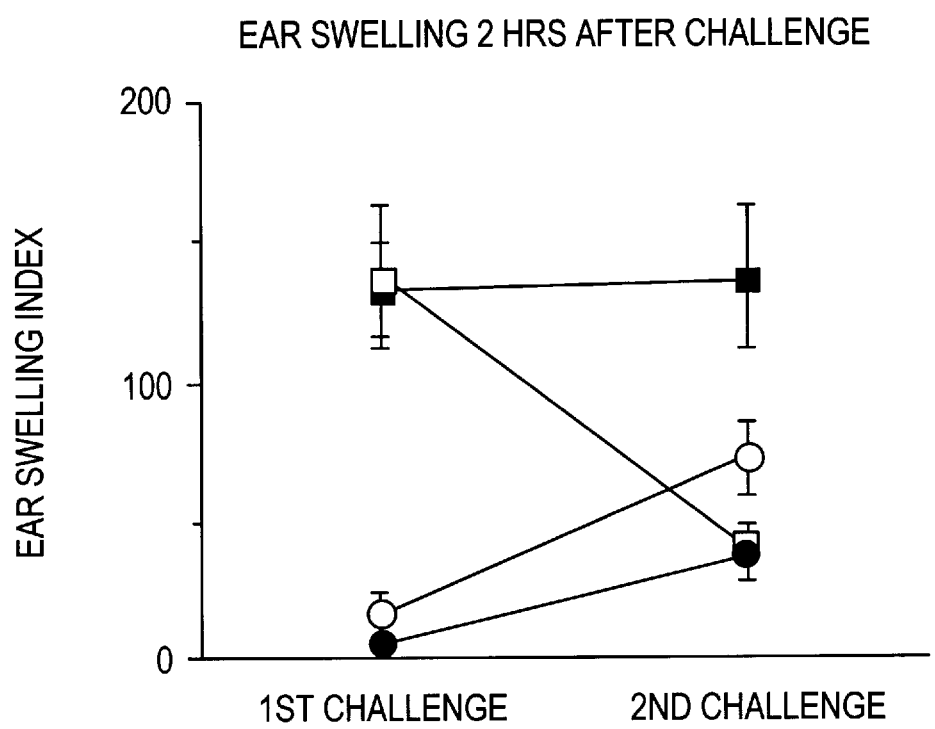
FIG. 11 graphically shows an inhibitory effect of sFcεRIα on secondary allergic reaction obtained in Test Example 6-B.

The results are shown in FIG. 11. At 2 hours after the first antigen challenge, there was no difference between the control group and the human sFceRIα-treated group. At 2 hours after the second antigen challenge, however, whereas the control mice showed ear swelling in a degree comparable to that after the first antigen challenge, the ear swelling reaction was inhibited in the mice treated with sFceRIα.

The above findings show that sFceRIα completely inhibits allergic reactions due to the second exposure and suggests it will do the same following further exposures to the antigen in patients with allergy and is, therefore, a very satisfactory prophylactic drug.

Test Example 7
Inhibitory effect of purified human sFceRIα on IgE production

Peripheral blood mononuclear cells (PBMC) derived from a healthy adult were treated with acidic buffer (pH 4.0) and adhesive monocytes were removed using a Petri dish. Then, B cells were isolated and purified by the rosette method using sheep erythrocytes and the panning method using anti-CD3 monoclonal antibody. PBMC was stimulated with interleukin-4 (IL-4, 100 U/ml) or pokeweed mitogen (PWM, 0.1 μg/ml) and B cells were stimulated with a combination of IL-4 and anti-CD40 monoclonal antibody (1 μg/ml) or a combination of IL-4 and hydrocortisoyne (HC, 1 μM), for 14 days. Each class of immunoglobulin produced in each culture supernatant was assayed by isotype-specific solid phase sandwich RIA. IgE assay was carried out using two anti-IgE monoclonal antibodies whose binding-activity to IgE was not inhibited concentration-dependently by purified human sFceRIα.

After stimulation of B cells with IL-4 for 3 days or with a combination of IL-4 and anti-CD40 monoclonal antibody for 10 days, total RNA was extracted from each group of cells and subjected to Northern blotting using cDNA probe specific for Cε2–Cε4 to examine as to how CεmRNA was expressed. Markers on the B cell surface were examined using a fluorescence activated cell sorter. The binding test of purified human sFceRIα to IgE was carried out using anti-sFceRIα monoclonal antibody which did not bind to IgE.

Figure 12:
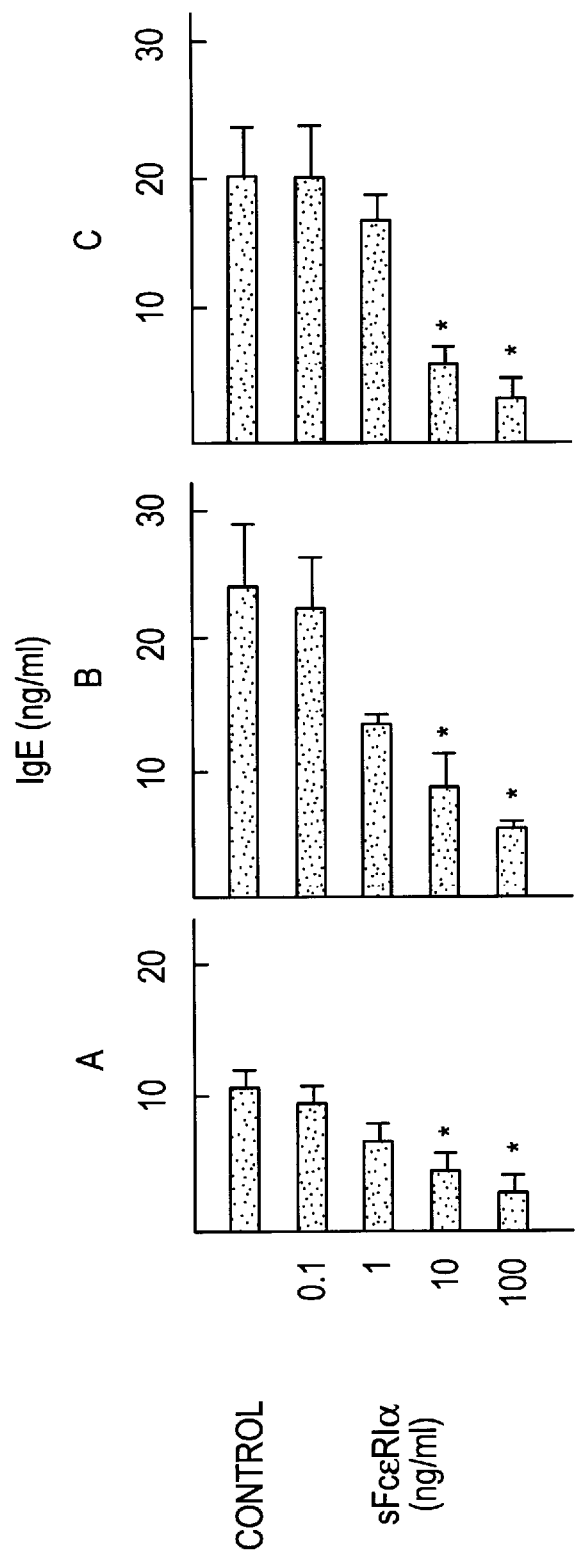
FIG. 12(A–C) is a graph showing inhibitory effect of purified sFcεRIα on the IgE production in human peripheral blood mononuclear cells (PBMC) stimulated with IL-4 (A), in B cells stimulated with IL-4 and anti-CD40 monoclonal antibody (B) or IL-4 and hydrocortisone (HC).
Figure 13:
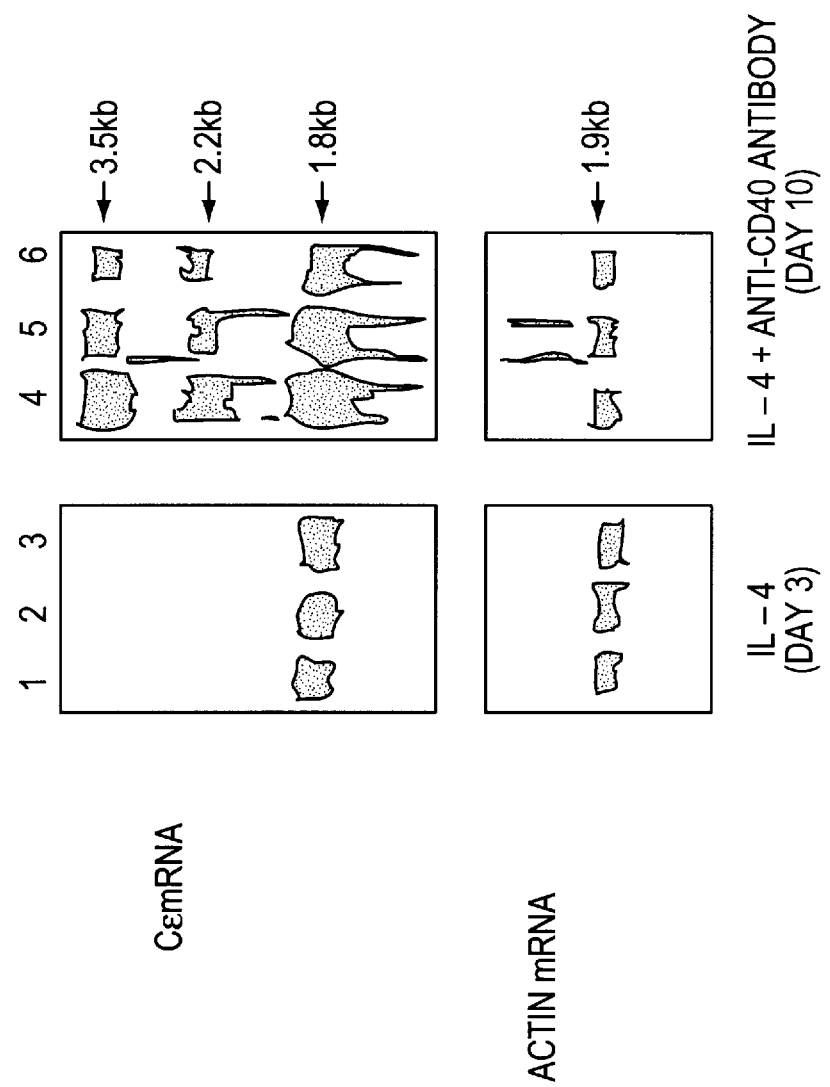
FIG. 13 is an electrophoretic pattern showing the effect of purified sFcεRIα on expression of CεmRNA in cultured B cells.

As a result, the IgE production in PBMC stimulated with IL-4 and B cells stimulated with a combination of IL-4 and anti-CD40 monoclonal antibody or a combination of IL-4 and HC was inhibited concentration-dependetly by 1 to 100 ng/ml of purified sFceRIα. The IgE production was statistically significantly inhibited by purified sFceRIα at a concentration ranging from 10 to 100 ng/ml ($p < 0.05$, paired t-test) (FIG. 12). Thus, from the results that purified sFceRIα inhibited the IgE production in both of T cell-dependent system and T cell-independent system, it was confirmed that a target cell of sFceRIα was B cell. In the case that B cells were stimulated with a combination of IL-4 and anti-CD40 monoclonal antibody, purified human sFceRIα inhibited expression of secretory CεmRNA (2.2 kb) at a concentration of from 10 to 100 ng/ml. On the other hand, in the case that B cells were stimulated with IL-4 alone, sFceRIα showed no effect on the expression of germline CεmRNA (1.8 kb) (FIG. 13).

It was also found that purified human sFceRIα did not affect the expression of various markers on the surface of the B cell stimulated with IL-4, including a low affinity IgE receptor FceRII (CD23), CD40, HLA-DR, IgM and IL-4 receptor and it did not inhibit liberation of soluble CD23 (sCD23). Further, the inhibitory effect of anti-CD23 monoclonal antibody against the IgE production in B cells was not affected by purified human sFceRIα. However, purified human sFceRIα reduced the IgE production of B cells enhanced by 29 kd sCD23 to the normal level or less.

Furthermore, purified human sFceRIα did not bind to T cells, B cells, NK cells and monocytes derived from a healthy adult as well as IgE non-producing B cell lines (e.g., RPMI1788, RPMI8866, Daudi), while it bound to IgE-producing human myeloma cell (U266). The excess amount of IgE dissociated the bonding between purified human sFceRIα and the myeloma cell.

Figure 14:
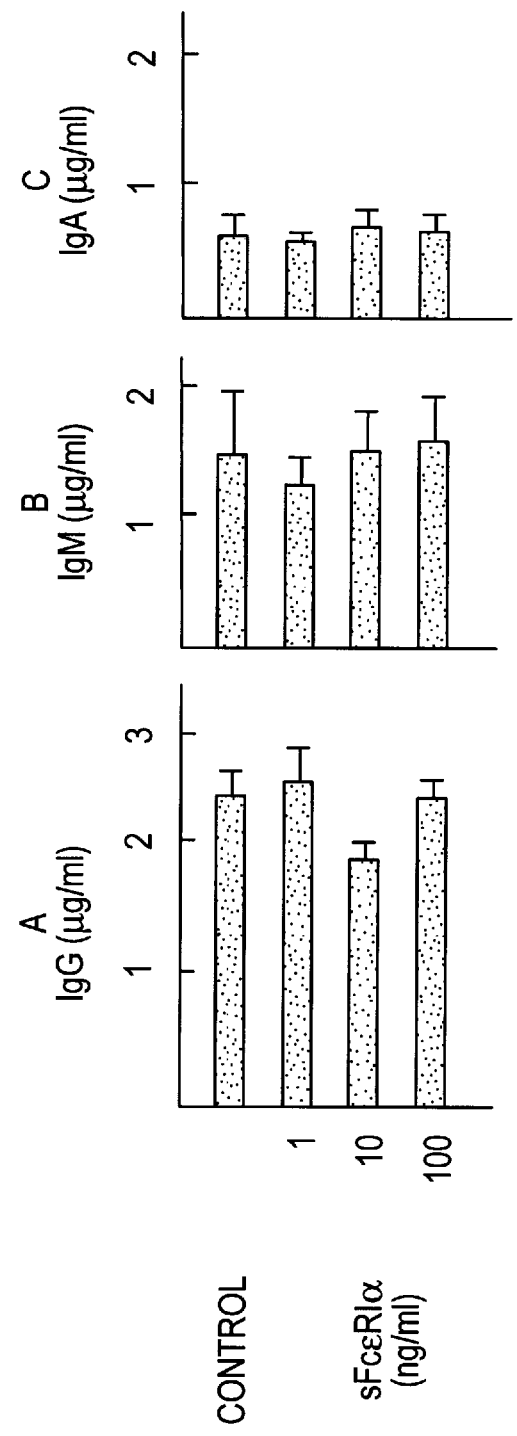
FIG. 14(A–C) is a graph showing the effect of purified sFcεRIα on production of IgG (A), IgM (B) and IgA (C) in peripheral blood mononuclear cells (PBMC) stimulated with pokeweed mitogen (PWM).

On the other hand, purified human sFceRIα did not prevent the production of IgG, IgM and IgA in PBMC stimulated with PWM (FIG. 14).

From these results, it was found that purified human sFceRIα was a novel molecule capable of specifically inhibiting production of IgE class antibodies.

While the invention has been described in detail and with reference to specific embodiments thereof, it will be apparent to one skilled in the art that various changes and modification can be made therein without departing from the spirit and scope thereof.

What is claimed is:

1. A method of inhibiting a secondary allergic response to an antigen in a human previously exposed to said antigen and requiring said inhibiting, said method comprising:

administering to said human an amount sufficient for inhibiting a secondary allergic response of an antiallergic composition which comprises, as an active ingredient, a peptide consisting of a high-affinity, human immunoglobulin E receptor α-chain or a soluble fragment thereof wherein said peptide is capable of binding to human IgE and thereby inhibiting a secondary allergic response in a human to said antigen.

2. The method of inhibiting an allergic response as claimed in claim 1, wherein said allergic response is anaphylactic shock, pollen allergy, atopic dermatitis or bronchial asthma.

3. A method of treating a secondary allergic response in a human requiring said treatment comprising inhibiting a secondary allergic reaction by administering to a human suffering from said allergic response an amount sufficient for treating a secondary allergic response of an antiallergic composition which comprises, as an active ingredient, a high-affinity human immunoglobulin E receptor α-chain or a soluble fragment thereof, which is capable of binding to human IgE and thereby mitigating said secondary allergic response in said human.

4. The method of treating an allergic response as claimed in claim 3, wherein said allergic response is anaphylactic shock, pollen allergy, atopic dermatitis or bronchial asthma.

5. A method of decreasing production of IgE in a human which comprises:

administering to a human a composition, comprising as an active ingredient, a peptide consisting of a high-affinity human immunoglobulin E receptor α-chain or a soluble fragment thereof capable of binding to human IgE in an amount sufficient to interact with activated B cells for inhibiting production of IgE and inhibiting production of IgE.

6. The method of claim 5, wherein production of IgE by said human is decreased sufficiently to prevent an allergic response in said human.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:1:

```
CCTCAACATT ACTGTAATAA AAGCTTAAG                                               29
```

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:2:

```
GATCCTTAAG CTTTTATTAC AGTAATGTTG AGGGGC                                       36
```

( 2 ) INFORMATION FOR SEQ ID NO:3:

( i ) SEQUENCE CHARACTERISTICS:
        ( A ) LENGTH: 713 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 120..713
        ( C ) IDENTIFICATION METHOD: by similarity with known
            sequence or to an established consensus ( x i ) SEQUENCE DESCRIPTION: SEQ ID NO:3:

```
AATTCCTCCA TGCTACTAAG AGTCTCCAGC ATCCTCCACC TGTCTACCAC CGAGCATGGG              60

CCTATATTTG AAGCTTAGA TCTCTCCAGC ACAGTAAGCA CCAGGAGTCC ATGAAGAAG               119

ATG GCT CCT GCC ATG GAA TCC CCT ACT CTA CTG TGT GTA GCC TTA CTG               167
Met Ala Pro Ala Met Glu Ser Pro Thr Leu Leu Cys Val Ala Leu Leu
 1               5                   10                  15

TTC TTC GCT CCA GAT GGC GTG TTA GCA GTC CCT CAG AAA CCT AAG GTC               215
Phe Phe Ala Pro Asp Gly Val Leu Ala Val Pro Gln Lys Pro Lys Val
             20                  25                  30

TCC TTG AAC CCT CCA TGG AAT AGA ATA TTT AAA GGA GAG AAT GTG ACT               263
Ser Leu Asn Pro Pro Trp Asn Arg Ile Phe Lys Gly Glu Asn Val Thr
         35                  40                  45

CTT ACA TGT AAT GGG AAC AAT TTC TTT GAA GTC AGT TCC ACC AAA TGG               311
Leu Thr Cys Asn Gly Asn Asn Phe Phe Glu Val Ser Ser Thr Lys Trp
     50                  55                  60

TTC CAC AAT GGC AGC CTT TCA GAA GAG ACA AAT TCA AGT TTG AAT ATT               359
```

-continued

```
Phe His Asn Gly Ser Leu Ser Glu Glu Thr Asn Ser Ser Leu Asn Ile
 65                  70                  75                  80

GTG AAT GCC AAA TTT GAA GAC AGT GGA GAA TAC AAA TGT CAG CAC CAA     407
Val Asn Ala Lys Phe Glu Asp Ser Gly Glu Tyr Lys Cys Gln His Gln
                 85                  90                  95

CAA GTT AAT GAG AGT GAA CCT GTG TAC CTG GAA GTC TTC AGT GAC TGG     455
Gln Val Asn Glu Ser Glu Pro Val Tyr Leu Glu Val Phe Ser Asp Trp
            100                 105                 110

CTG CTC CTT CAG GCC TCT GCT GAG GTG GTG ATG GAG GGC CAG CCC CTC     503
Leu Leu Leu Gln Ala Ser Ala Glu Val Val Met Glu Gly Gln Pro Leu
        115                 120                 125

TTC CTC AGG TGC CAT GGT TGG AGG AAC TGG GAT GTG TAC AAG GTG ATC     551
Phe Leu Arg Cys His Gly Trp Arg Asn Trp Asp Val Tyr Lys Val Ile
    130                 135                 140

TAT TAT AAG GAT GGT GAA GCT CTC AAG TAC TGG TAT GAG AAC CAC AAC     599
Tyr Tyr Lys Asp Gly Glu Ala Leu Lys Tyr Trp Tyr Glu Asn His Asn
145                 150                 155                 160

ATC TCC ATT ACA AAT GCC ACA GTT GAA GAC AGT GGA ACC TAC TAC TGT     647
Ile Ser Ile Thr Asn Ala Thr Val Glu Asp Ser Gly Thr Tyr Tyr Cys
                165                 170                 175

ACG GGC AAA GTG TGG CAG CTG GAC TAT GAG TCT GAG CCC CTC AAC ATT     695
Thr Gly Lys Val Trp Gln Leu Asp Tyr Glu Ser Glu Pro Leu Asn Ile
            180                 185                 190

ACT GTA ATA AAA GCT TAA                                             713
Thr Val Ile Lys Ala
        195
```